(12) United States Patent
Zhang et al.

(10) Patent No.: US 7,732,126 B2
(45) Date of Patent: Jun. 8, 2010

(54) INTEGRIN CD18 IS A NOVEL STROMAL STEM CELL MARKER AND FUNCTIONS TO PROMOTE OSTEOGENESIS

(75) Inventors: Li Zhang, Boyds, MD (US); Yasuo Miura, Kyoto (JP); Songtao Shi, Irvine, CA (US)

(73) Assignee: University of Maryland, Baltimore, Baltimore, MD (US)

( * ) Notice: Subject to any disclaimer, the term of this patent is extended or adjusted under 35 U.S.C. 154(b) by 437 days.

(21) Appl. No.: 11/574,581

(22) PCT Filed: Sep. 6, 2005

(86) PCT No.: PCT/US2005/032220
§ 371 (c)(1),
(2), (4) Date: Mar. 1, 2007

(87) PCT Pub. No.: WO2006/029347
PCT Pub. Date: Mar. 16, 2006

(65) Prior Publication Data
US 2007/0248998 A1    Oct. 25, 2007

Related U.S. Application Data

(60) Provisional application No. 60/606,982, filed on Sep. 3, 2004, provisional application No. 60/690,767, filed on Jun. 15, 2005.

(51) Int. Cl.
*A01N 1/02* (2006.01)

(52) U.S. Cl. .................... 435/2; 435/1.1; 435/7.21; 435/372; 435/287.2; 436/526; 436/540; 436/63; 436/177

(58) Field of Classification Search ................. 435/1.1, 435/7.21, 7.23, 7.24, 7.94, 372, 287.1; 436/526, 436/540, 10, 56, 64, 161, 172, 177; 422/73, 422/82.05, 82.09, 101
See application file for complete search history.

(56) References Cited

U.S. PATENT DOCUMENTS 6,528,245 B2    3/2003  Sanchez-Ramos et al.

(Continued)

OTHER PUBLICATIONS

Gunji et al., Expression and Function of Adhesion Molecules on Human Hematopoitic Stem Cells: CD34+ LFA-1-Cells are More Primitive than CD34+ LFA-1+ Cells, Blood 80 (2): 42-436 (Jul. 15, 1992).*

(Continued)

*Primary Examiner*—Gailene R Gabel
(74) *Attorney, Agent, or Firm*—Ditthavong Mori & Steiner, P.C.

(57) ABSTRACT

The present invention is directed to a new bone marrow stromal stem cell (BMSSC) marker, CD18, for use in selecting a population of cells enriched in BMSSCs, from bone marrow cells, adipose cells, or peripheral blood. The invention is further directed to methods for selecting a population of cells enriched in BMSSCs based on the selective expression of CD18 on their surface, using techniques known in the art such as fluorescent assisted cell sorting, an immunomagnetic method, flow microfluorimetry, immunofluorescence, immunoperoxidase staining, radioimmunoassay and immunoaffinity chromatography. The invention is further directed to the BMSSCs isolated based on CD18 expression, and their use to treat various diseases. In one aspect, the HMSSCs are transformed with a vector having a normal gene for CD18, and the transformed BMSSCs are administered to treat bone degenerative diseases and diseases of bone involving abnormal expression of CD18 expression of CD18.

20 Claims, 6 Drawing Sheets

U.S. PATENT DOCUMENTS 7,122,178 B1 * 10/2006 Simmons et al. ............ 424/93.1
2005/0019911 A1 1/2005 Gronthos et al.

OTHER PUBLICATIONS

Tani-Ishii N. Penn1nger et al., The role of LFA-1 in osteoclast development induced by co-cultures of mouse bone marrow cells and MC3T3-G2/PA6 cells, J Periodont Res (2002) 37:184-191.*

Stan Gronthos, et al., The STRO-1+ Fraction of Adult Human Bone Marrow Contains the Osteogenic Precursors Journal of Cell Science 116, 1827-1835 © 2003.

Stan Gronthos, et al, The STRO-1+ Fraction of Adult Human Bone Marrow Contains the Osteogenic Precursors Blood, vol. 84, No. 12, (Dec. 15, 1994): pp. 4164-4173.

M, Hai.,, et al., Retroviral-Mediated Gene Transfer of CD18 into Hematopoietic Stem Cells in Dogs with Canine Leukocyte Adhesion Deficiency Reverses the Severe Deficiency Phenotype, *Blood* (ASH Annual Meeting Abstracts) 2004 104: Abstract 3169.

James E. Dennis, et al., The STRO-1+ Marrow Cell Population is Multipotential, Cells Tissues Organs 2002;170:73-82.

P. Van Vlasselaer, , et al, Characterization and Purification of Osteogenic Cells From Murine Bone Marrow by Two-Color Cell Sorting Using Anti-Sca-1 Monoclonal Antibody and Wheat Germ Agglutinin, *Blood*, vol. 84, No. 3 (Aug. 1), 1994: pp. 753-763.

Tani-Ishii N. Penninger, et al., The role of LFA-1 in osteoclast development induced by co-cultures of mouse bone marrow cells and MC3T3-G2/PA6 cells, J Periodont Res 2002; 37; 184-191.

Songtao Shi, Perivascular Niche of Postnatal Mesenchymal Stem Cells in Human Bone Marrow and Dental Pulp, Journal of Bone and Mineral Research, vol. 18, No. 4, 2003.

Daniel Howard, et al., Immunoselection and adenoviral genetic modulation of human osteoprogenitors: in vivo bone formation on PLA scaffold, Biochemical and Biophysical Research Communications 299 (2002) 208-215.

Kevin P. McHugh, et al., Mice lacking $\beta 3$ integrins are osteosclerotic because of dysfunctional osteoclasts, *J. Clin. Invest.* 105:433-440 (2000).

Karin Scharffetter-Kochanek, Spontaneous Skin Ulceration and Defective T Cell, J. Exp. Med., vol. 188, No. 1, Jul. 6, 1998 119-1.

Gunji et al. (Expression and Function of Adhesion Molecules on Human Hemeopoietic Stem Cells: CD34+LFA—Cells are more Primitive than CD34+LFA-Cells, Blood. (1992) vol. 80, No. 2, pp. 429-436, see Abstract and pp. 429-438.

Stewart et al. STRO-1, HOP-26 (CD63), CD49a and SB-10 (CD166) as markers of primitive human marrow stromal cells and their more differentiated progeny; a comparative investigation in vitro, Cell Tissue Res. 2003. vol. 313, pp. 281-290, see Abstract and pp. 281-283.

\* cited by examiner

INTEGRIN CD18 IS A NOVEL STROMAL STEM CELL MARKER AND FUNCTIONS TO PROMOTE OSTEOGENESIS

CROSS-REFERENCE TO RELATED APPLICATIONS

This application claims the benefit of Provisional Application No. 60/606,982, filed Sep. 3, 2004, and Provisional Application No. 60/690,767, filed Jun. 15, 2005, the entire contents of which are hereby incorporated by reference as if fully set forth herein, under 35 U.S.C. §119(e).

STATEMENT OF GOVERNMENTAL INTEREST

This invention was made with Government support under Grant # HL61589. The Government has certain rights in the invention. This invention was also kindly supported with funds from the American Heart Association, Grant no. 0240208N.

BACKGROUND OF THE INVENTION

1. Field of the Invention

The present invention relates to cell surface proteins on bone marrow stromal stem cells (BMSSCs), in particular CD18, which can be used as a marker for making stem cell enriched extracts from unfractionated bone marrow aspirates and from other sources such as adipose tissue. The invention also relates to methods of using the BMSSCs for the treatment of diseases, especially bone marrow diseases.

2. Description of the Related Art

Bone marrow contains stem-like precursors for non-hematopoietic cells, such as osteoblasts, chondrocytes, adipocytes and myoblasts (Owen et al., 1988, in Cell and Molecular Biology of Vertebrate Hard Tissues, Ciba Foundation Symposium 136, Chichester, UK, pp. 42-60; Caplan, 1991, J. Orthop. Res 9:641-650; Prockop, 1997, Science 276:71-74). Non-hematopoietic precursors of the bone marrow have been variously referred to as colony-forming-unit-fibroblasts, mesenchymal stem cells, and bone marrow stromal stem cells (BMSSCs). BMSSCs are believed to participate in the creation of the microenvironment within the bone marrow in vivo. When isolated, BMSSCs are initially quiescent but eventually begin dividing so that they can be cultured in vitro. Expanded numbers of stromal cells can be established and maintained. Stromal cells have been used to generate colonies of fibroblastic adipocytic and osteogenic cells when cultured under appropriate conditions. They can also be made to differentiate into cartilage cells and myoblasts.

There are several examples of the use of BMSSCs for treatment of disease. Stromal cells have been used to produce fibrous tissue, bone or cartilage when implanted into selective tissues in vivo (Ohgushi et al., 1989, Acte. Orthop. Scand. 60:334-339; Nakahara et al., 1992, J. Orthop. Res 9:465-476; Niedzwiedski et al., 1993, Biomaterials 14:115-121; and Wakitani et al., 1994, J. Bone & Surg. 76A:579-592). In some reports, stromal cells have been used to generate bone or cartilage in vivo when implanted subcutaneously with a porous ceramic (Ohgushi, et al., 1989, Acta Orthop. Scand. 60:334-339), intraperitoneally in a diffusion chamber (Nakahara et al., 1991, J. Orthop. Res 9:465-476), percutaneously into a surgically induced bone defect (Niedzwiedski, et al., 1993, Biomaterials 14: 115-121), or transplanted within a collagen gel to repair a surgical defect in a joint cartilage (Wakitani et al., 1994, J. Bone Org. 76A: 579-592). Piersma et al. (1983, Brit. J. Hematol. 94:285-290) disclose that after intravenous bone marrow transplantation, the fibroblast colony-forming cells which make up the hemopoietic stroma lodge and remain in the host bone marrow. Stewart et al. (1993, Blood 81:2566-2571) recently observed that unusually large and repeated administrations of whole marrow cells produced long-term engraftment of hematopoietic precursors into mice that had not undergone marrow ablation. Also, Biennzle et al. (1994, Proc. Natl. Acad. Sci. USA, 91:350-354) successfully used long-term bone marrow cultures as donor cells to permanently populate hematopoietic cells in dogs without marrow ablation. In some reports, stromal cells were used either as cells that established a microenvironment for the culture of hematopoietic precursors (Anklesaria, 1987, PNAS USA 84:7681-7685) or as a source of an enriched population of hematopoietic stem cells (Kiefer, 1991, Blood 78(10):2577-2582).

This new research has shown that adult stem cells in fact possess much wider potential for differentiation than previously thought. The identification and isolation of the stem cells enables the reinfusion of these long-term repopulating stem cells in various clinical therapies. For example, purging bone marrow stem cells of contaminating tumor cells would require reintroduction of new uncontaminated stem cells. In gene therapy, stem cells either from a patient or a donor can be transfected to contain new genes of therapeutic use and then reintroduced into the patient. Identification of surface markers on stem cells is extremely useful in hematopoietic research and related therapies because such markers allow the isolation of relatively pure populations of immature stem cells. However, the lack of appropriate surface markers has been a major obstacle for incorporating bone marrow stromal stem cells (BMSSCs) in clinical applications.(4) At present the only useful marker for this purpose is STRO-1. Thus, there is a continued need for the identification other antigens on BMSCCs to simplify the identification and separation of these cells from bone marrow aspirates (or from peripheral blood or adipose tissue which also have BMSSCs).

DEFINITIONS

The term "CD18" refers to the $\beta_2$ integrins, including $\alpha_L\beta_2$, $\alpha_M\beta_2$, $\alpha_X\beta_2$ and $\alpha_D\beta_2$. CD18 is a cell adhesion molecule.

The term "BMSSC" means bone marrow stem cells. BMSSCs include those bone marrow stem cells that express the CD18 antigen, among other surface antigens, and include pluripotent stem cells. A cell is operationally defined as CD18-positive if it expresses sufficient CD18 antigen to be detected by a given method of assay including flow microfluorimetry using a fluorescence-activated cell sorter (FACS), immunofluorescence or immunoperoxidase staining using a fluorescence or light microscope, fluorescence-activated cell sorting, immunoblotting, panning (Wysocki and Sato, Proc. Natl. Acad. Sci. (USA) 75: 2844, 1978), radioimmunoassay, immunoaffinity chromatography (Basch et al., J. Immunol. Methods 56: 269, 1983), magnetic-activated cell sorting (Miltenyi et al., Cytometry 11:231, 1990), and cytolysis, among numerous other methods which will be readily apparent to one skilled in the art (see, for example, Lansdorp and Thomas in Bone Marrow Processing and Purging, A. P. Gee (ed.), Boca Raton: CRC Press (1991) pg. 351), the entire contents of which are hereby incorporated by reference as if fully set forth herein, under 35 U.S.C. §119(e).

The term "osteogenic differentiation of BMSSCs" refers to a process by which BMSSCs become osteoblastic cells and form bone tissue under defined in vitro culture conditions or in vivo microenvironment. Part of normal osteogenic differentiation of BMSSCs requires osteogenic master protein Cbfa1.

The term "osteoclastic activity" refers to the bone resorption activity associated with osteoclasts.

The term "Hematopoiesis-supportive" refers to the function of BMSSCs in supporting hematopoietic cells growth and survival in vitro and in vivo.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1 FIG. 1A shows expression of CD18 on mouse BMSSCs by fluorescence assisted cell sorting analysis (FACS) using monoclonal antibodies (mAbs) against CD18 (on the Y axis) with one mAb from the group Sca-1, CD14, CD34 and FITC-IgG1 (on the X axis). FIG. 1B shows immunoblot analyses of murine and human BMSSCs. Equal protein loading was confirmed by reprobing with mAbs specific for β-actin or α-actinin. The data shown are representative of two independent experiments.

FIG. 2A shows two distinct human cell populations collected by FACS (R2: STRO-1$^{bright}$/CD18$^+$ and R3: STRO-1$^{bright}$/CD18$^-$). FIG. 2B shows CFU-F assays of the cells in FIG. 2A. FIG. 2C shows the phenotypic characterization of human R2 STRO-1$^{bright}$/CD18$^+$ BMSSCs by FACS analysis using different lineage-specific mAb. Their corresponding isotype-matched non-immune IgGs were used as controls (bold line). FIG. 2D shows the differentiation potential of the STRO-1$^{bright}$/CD18$^+$ BMSSCs cultured in vitro under adipogenic induction condition for 2 weeks (a), osteogenic induction condition for 3 weeks (b), and chondrogenic induction condition for 3 weeks (c). Oil Red O staining demonstrates the generation of lipid-laden adipocytes (arrows) (a); Alizarin Red S staining shows mineral deposits (arrows) made by osteogenic cells (b); and Alcian blue staining of the cartilage matrix deposition (arrows) demonstrates the chondrogenic differentiation in aggregate cultures (c). The data shown are representative of two independent experiments. Magnification: a-b, ×400; c, ×64.

FIG. 3A is Faxitron analysis demonstrating a decreased bone density in the femurs of 5 week-old CD18$^{-/-}$ mice (KO, right) as compared to their WT counterparts (left). FIG. 3B is DXA analysis of the femurs from 15-week-old mice showing a statistically significant difference in BMD between WT (left) and CD18$^{-/-}$ (right) mice ($p=0.025$, $n=4$). FIG. 3C shows hematoxylin and eosin staining on the metaphysis area of the femurs. Magnification 400×. FIG. 3D is representative images of the distal femur metaphysis on micro-computed tomography analysis showing decreased bone volume, trabecular bone number, trabecular bone thickness, and an increased trabecular bone space. FIG. 3E is alizarin red and alcian blue double skeletal staining for bone and cartilage of 1-week-old mice. WT, wild type; KO, CD18$^{-/-}$.

FIG. 5 FIG. 5A shows in vitro mineralization induction of CD18$^{-/-}$ BMSSCs determined by Alizarin red S staining (magnification ×10) compared to WT cells ($p=0.00003$, $n=3$ mice). The total mineralized area by WT cells was assigned to 100%. FIG. 5B shows cell adhesion of CD18$^{-/-}$ BMSSCs compared to WT. FIG. 5C shows proliferation of BMSSCs evaluated by BrdU incorporation with the percentage of BrdU$^+$ cells determined manually by counting 10 representative fields. ($p=0.01$, $n=3$ mice). FIG. 5D shows the number of BMSSC colonies obtained from $10^6$ bone marrow cells for CD18$^{-/-}$ mice vs. WT ($p=0.0064$, $n=6$ mice). Magnification ×10.

FIG. 6 FIG. 6A shows Cbfa1 expression and Smad2 phosphorylation by immunoblot. Equal protein loading was verified by reprobing with an α-actinin-specific mAb. The data shown are representative of three independent experiments FIG. 6B shows immunoblots of retroviral-mediated expression of recombinant CD18 using an anti-CD18 cytoplasmic tail antibody, which does not react with CD18 (CT–) well. CD18$^{-/-}$ BMSSCs were infected with retroviral supernatants encoding either full length CD18 or the cytoplasmic tail-truncated CD18 (CT–) for 6 days Non-infected WT and CD18$^{-/-}$ BMSSCs were included as controls. Protein loading was shown by reprobing for α-actinin. FIG. 6C shows bone formation in vivo. WT, CD18$^{-/-}$, and retroviral infected CD18$^{-/-}$ BMSSCs with either full length CD18 or truncated CD18 (CT–) were mixed with HA/TCP and then implanted in nude mice subcutaneously. BMSSC-mediated bone formation was analyzed 7 weeks post-implantation by hematoxylin and eosin staining. Staining was quantified using the software NIH Image based on five representative areas, and was expressed as a percentage of bone formation by WT BMSSCs, ($p=0.008$, $n=4$ mice). B=newly formed bone; HA=hydroxyapatite/tricalcium phosphate; and CT=connective tissues, Magnification ×200. FIG. 6D shows restoration of the osteogenic capability of the CD18$^{-/-}$ BMSSCs. ($p=0.0001$, $n=4$ mice) but not CD18 (CT–) ($p=0.39$, $n=4$ mice).

SUMMARY OF THE INVENTION

Figure 1:
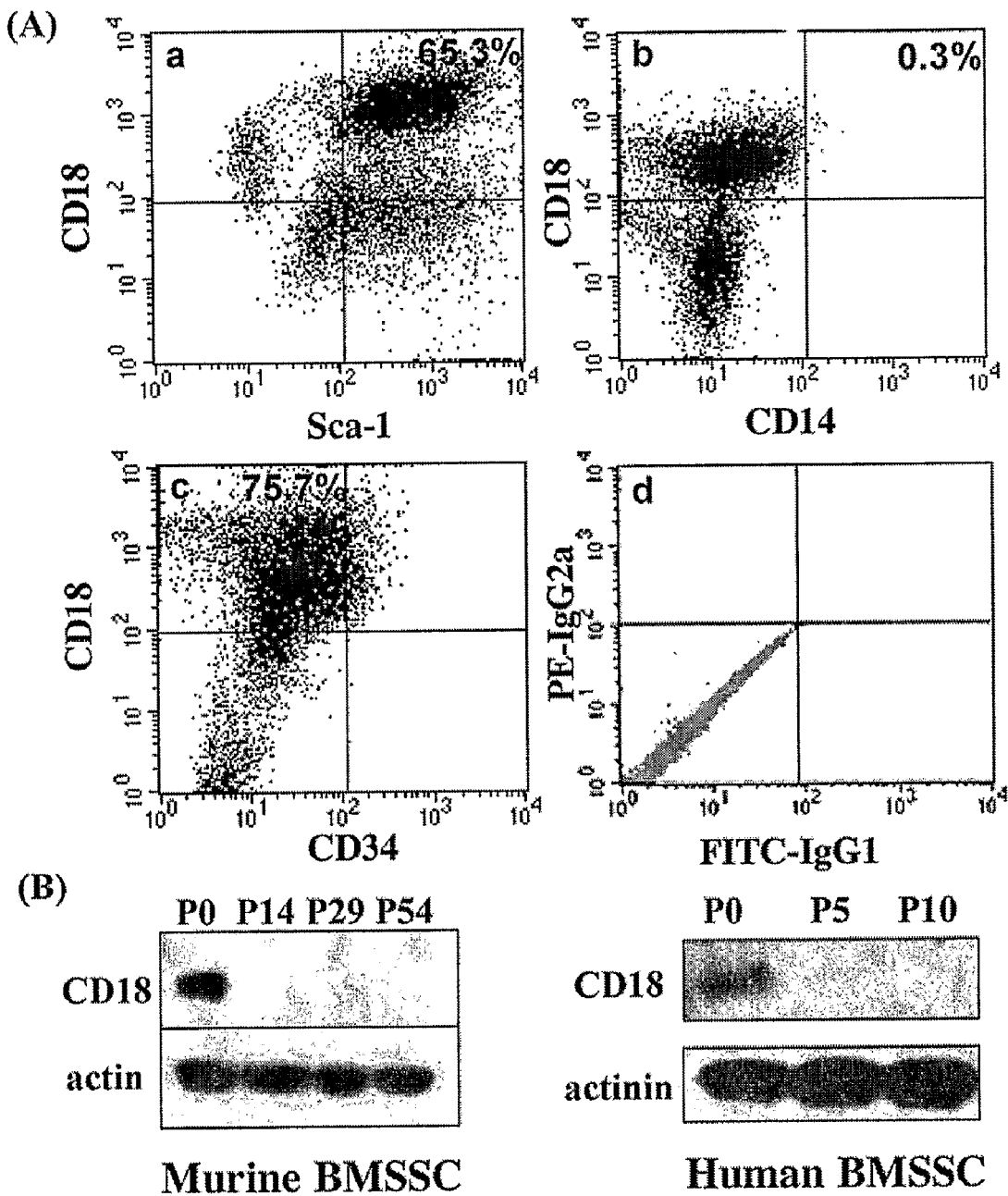

In one aspect of the invention, a population of animal cells enriched in bone marrow stromal stem cells that express the CD18 antigen is produced by: obtaining a sample of bone marrow from the animal, selecting bone marrow mononuclear cells from the sample, contacting the bone marrow mononuclear cells of step (b) with a reagent that binds to the CD18 antigen under conditions that permit the reagent and the CD18 antigen to bind; and selecting the bone marrow mononuclear cells that are bound to the reagent, thereby obtaining the population of animal cells enriched in bone marrow stromal stem cells that express the CD18 antigen. In another preferred embodiment a population of animal cells enriched in bone marrow stromal stem cells are selected by: obtaining a sample of bone marrow from the animal, (b) selecting bone marrow mononuclear cells from the sample, (c) contacting the bone marrow mononuclear cells of step (b) with a first reagent that binds to the STRO-1 antigen under conditions that permit the first reagent and the STRO-1 antigen to bind; (d) selecting the bone marrow mononuclear cells that are bound to the first reagent, thereby obtaining bone marrow stromal stem cells that express the STRO-1 antigen, (e) contacting cells of step (d) with a second reagent that binds to the CD18 antigen under conditions that permit the second reagent and the CD18 antigen to bind, and (f) selecting cells of step (e) to obtain bone marrow stromal stem cells that express both the CD18 and STRO-1 antigens, thereby obtaining the population of animal cells enriched in bone marrow stromal stem cells. The reagents are preferably antibodies directed against the BMSSC markers, but any agent that selectively binds to the BMSSC marker can be used. In an aspect, the reagents are labeled for easy detection, for example with fluorescent markers.

In an aspect of the invention, BMSSCs are derived from peripheral blood or adipocytes. In an aspect of the invention, the BMSSC-enriched population is obtained using fluorescent assisted cell sorting, an immunomagnetic method, flow microfluorimetry, immunofluorescence, immunoperoxidase staining, radioimmunoassay or immunoaffinity chromatography. In another aspect the invention is directed to an isolated population of animal cells enriched in bone marrow stromal stem cells that express the CD18 antigen or both CD18 and the STRO-1 antigen produced according to the methods described herein.

An aspect of the invention is further directed to chondrocytes, adipocytes, neurons and osteoblasts derived from BMSSCs that were isolated using CD18 as a selection marker. Another aspect is directed to CD18 as a selection marker for isolating enriched populations of BMSSCs. Other aspects are directed to methods for treating bone marrow diseases, leukocyte adhesion deficiency I, and bone degenerative diseases by administering to a patient having the disease or at risk for developing the disease, BMSSCs that have been transformed with an expression vector having a normal gene for CD18. A further aspect includes bone marrow stem cells from an animal, which cells have been transformed with an expression vector having a normal gene for CD18.

DETAILED DESCRIPTION

It has been discovered that CD18 antigen is expressed on the surface of BMSSCs and can be used as a selective marker to obtain a population of animal cells enriched in bone marrow stromal stem cells. CD18 is also referred to in the literature as $\beta_2$ integrins of which there are four ($\alpha_L\beta_2$, $\alpha_M\beta_2$, $\alpha_X\beta_2$, and $\alpha_D\beta_2$). One embodiment of the present invention is directed to the use of CD18 as a BMSSC marker to isolate a population of animal cells enriched in bone marrow stromal stem cells using techniques known in the art such as fluorescent assisted cell sorting, an immunomagnetic method, flow microfluorimetry, immunofluorescence, immunoperoxidase staining, radioimmunoassay and immunoaffinity chromatography. An embodiment is directed to the BMSSC-enriched population of cells that is selected from a sample of the animal's bone bone marrow mononuclear cells (BMNCs) based on the selective expression of CD18 on the surface of BMSSCs and its binding to a reagent that specifically binds to CD18, such as an anti-CD18 antibody. Another embodiment is directed to a population of animal cells enriched in BMSSCs that is selected from a sample of the animal's bone marrow mononuclear cells (BMNCs) based on the selective expression of both CD18 and STRO-1 on the surface of BMSSCs, which population is selected based on the ability of BMSSCs to bind to both a first reagent that specifically binds to CD18 antigen, and to an second reagent that specifically binds to STRO-1 antigen. The invention is further directed to methods for obtaining these populations of BMSSC-enriched animal cells.

BMSSCs that express CD18 or CD18 and STRO-1 are pleuripotent, and are capable of differentiating into chondrocytes, osteoblasts or adipocytes. Some have reported that BMSSCs can also differentiate into neurons and muscle. Sanchez-Ramos, et al. have shown that bone marrow stromal cells (BMSC) differentiate into neuron-like phenotypes in vitro and in vivo, when engrafted into normal or denervated rat striatum. U.S. Pat. No. 6,528,245, the entire contents of which is incorporated by reference as if set forth fully herein. The BMSC did not remain localized to the site of the graft, but migrated throughout the brain and integrated into specific brain regions in various architectonic patterns. The most orderly integration of BMSC was in the laminar distribution of cerebellar Purkinje cells, where the BMSC-derived cells took on the Parkinje phenotype. The BMSC exhibited site-dependent differentiation and expressed several neuronal markers including neuron-specific nuclear protein, tyrosine hydroxylase and calbindin. BMSC can be used to target specific brain nuclei in strategies of neural repair and gene therapy.

Certain embodiments are therefore directed to chondrocytes, neurons, osteoblasts or adipocytes that differentiate from the population of cells enriched in BMSSCs that are isolated based on their expression of CD18 or CD18 and STRO-1.

Leukocyte Adhesion Deficiency type I (LADI) is a disease where one or more mutations occur in the CD18 subunit such that expression of all four CD18 integrins ($\alpha_L\beta_2$, $\alpha_M\beta_2$, $\alpha_X\beta_2$, and $\alpha_D\beta_2$) is abolished. Methods are provided for preventing or treating LADI in an animal by administering a population of cells enriched in BMSSCs that express normal CD18 antigen, which BMSSCs were isolated from the patient using the methods of the present invention from a healthy animal of the same species using CD18 as a selective marker. In another embodiment, the animal's own BMSSCs are isolated, transformed with an expression vector having gene for normal CD18, and reintroduced into the animal. In a preferred embodiment the animal is a human.

In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Bone marrow stromal stem cells are potentially involved in the replenishment of a wide range of cell types through an adult life, including osteoblasts, chondrocytes, adipocytes, and neural cells. U.S. Pat. No. 6,528,245. Thus, BMSSCs represent an easily accessible and renewable source of stem cells for tissue engineering to repair damaged tissues (18). In addition, osteoblasts derived from BMSSCs are critical to the maintenance of the niche microenvironment for hematopoiesis (1,2). However, due in part to the lack of specific surface markers for BMSSCs, their therapeutic use has been limited. It has now been discovered that CD18 is selectively expressed on bone marrow stromal stem cells a new and can be used as unique surface marker for separating BMSSCs from a heterogeneous population of cells, typically bone marrow mononuclear cells (BMNCs) in a sample of bone marrow. However, CD18 can also be used as a selective marker to separate BMSSCs from a population of adipose cells or peripheral blood cells. CD18 includes the four different heterodimeric receptors ($\alpha_L\beta_2$, $\alpha_M\beta_2$, $\alpha_X\beta_2$, and $\alpha_D\beta_2$), which are primarily expressed on cells of hematopoietic origin (3).

It has also been discovered that CD18 can be used together with STRO-1 as markers to separate BMSSCs from a heterogeneous population of cells, including BMNC in a bone marrow sample. Using CD18 in addition to STRO-1 enriched the population of isolated BMSSCs by a factor of 15 compared to the use of STRO-1 alone.

It was further discovered that genetic inactivation of CD18 in mice caused impaired osteogenic differentiation of BMSSCs through inhibition of osteogenic master protein Cbfa1 which leads to defective bone formation in vivo. CD18-deficient animals also showed decreased bone mineral density (BMD). By contrast, inactivation of CD18 had no significant effect on in vivo osteoclastic activity. The defective osteogenesis of the CD18-deficient BMSSCs was rescued by expression of full length but not a cytoplasmic domain-truncated CD18. This shows that CD18 is critical to the function of the BMSSCs; its deficiency causes a predisposition to bone defects. Mice lacking CD18 exhibit certain features of osteoporosis, including decreased bone marrow density (BMD), reduced trabecular bone number, decreased trabecular bone thickness, and increased trabecular bone space.

Osteoporosis is characterized by excessive loss of bone and deterioration of bone tissue, due to an overall imbalance between osteoblast-mediated bone formation and osteoblast-mediated bone resorption. Osteoblasts are derived from the BMSSCs (18), and play critical roles in the maintenance of bone mineral density (BMD) and in the formation of a bone marrow niche microenvironment that is essential for hematopoiesis (1, 2). When implanted subcutaneously, the BMSSCs are capable of forming ectopic bone and bone marrow (19). Given their osteogenic capability, the in vitro expanded BMSSCs have been successfully used clinically to repair fractured bones (20).

CD18 is Selectively Expressed on BMSSCs

The antigen CD18 is a known cell surface antigen on hematopoietic cells, however the selective presence of CD18 on the surface of BMSSCs (and progenitor cells in bone marrow was not known until this work was undertaken. BMSSCs can be obtained from fetal and adult bone marrow and can be separated using reagents and methods of the invention. BMSSCs can also be obtained from peripheral blood and adipose tissue. Efficient hematopoiesis occurs mainly in the bone marrow (BM) micro-environment and depends on cooperation between the bone marrow stromal stem cells (BMSSCs) and the hematopoietic stem cells (HSCs).

To examine whether CD18 is also expressed on BMSSCs, BMSSCs were isolated from wild type mice (mBMSSCs) under established culture conditions (19, 22) and from CD18-deficient mice. The isolated BMSSCs were grown in vitro for 23 days. Expression of CD18 on mouse BMSSCs (mBMSSCs) was demonstrated by fluorescence assisted cell sorting analysis (FACS) using monoclonal antibodies (mAbs) against CD18, plus one additional mAb from the group Sca-1 (astromal stem cell marker (29), CD14 (a commonly used macrophage marker), CD34 (a hematopoietic stem cell marker) and FITC-IgG1. BMSSCs that were derived directly from bone marrow without cell passage (i.e. passage 0), showed that a major cell population (about 65%) were double positive for CD18 and Sca-1 (astromal stem cell marker, (29)). FIG. 1A, panel a. Expression of CD18 was not due to contaminating macrophages as the CD18+ cells were negative for CD14, a commonly used macrophage marker (FIG. 1A, panel b). CD18+ cells also did not express CD34. FIG. 1A, panel c. Immunoblot analyses showed that both murine and human BMSSCs expressed CD18. In both cases, the CD18 expression level decreased upon consecutive cell passages (FIG. 1B). CD18 is thus a marker for early stage BMSSCs. Equal protein loading was confirmed by re-probing with mAbs specific for β-actin or α-actinin. The data shown are representative of two independent experiments.

Figure 2:
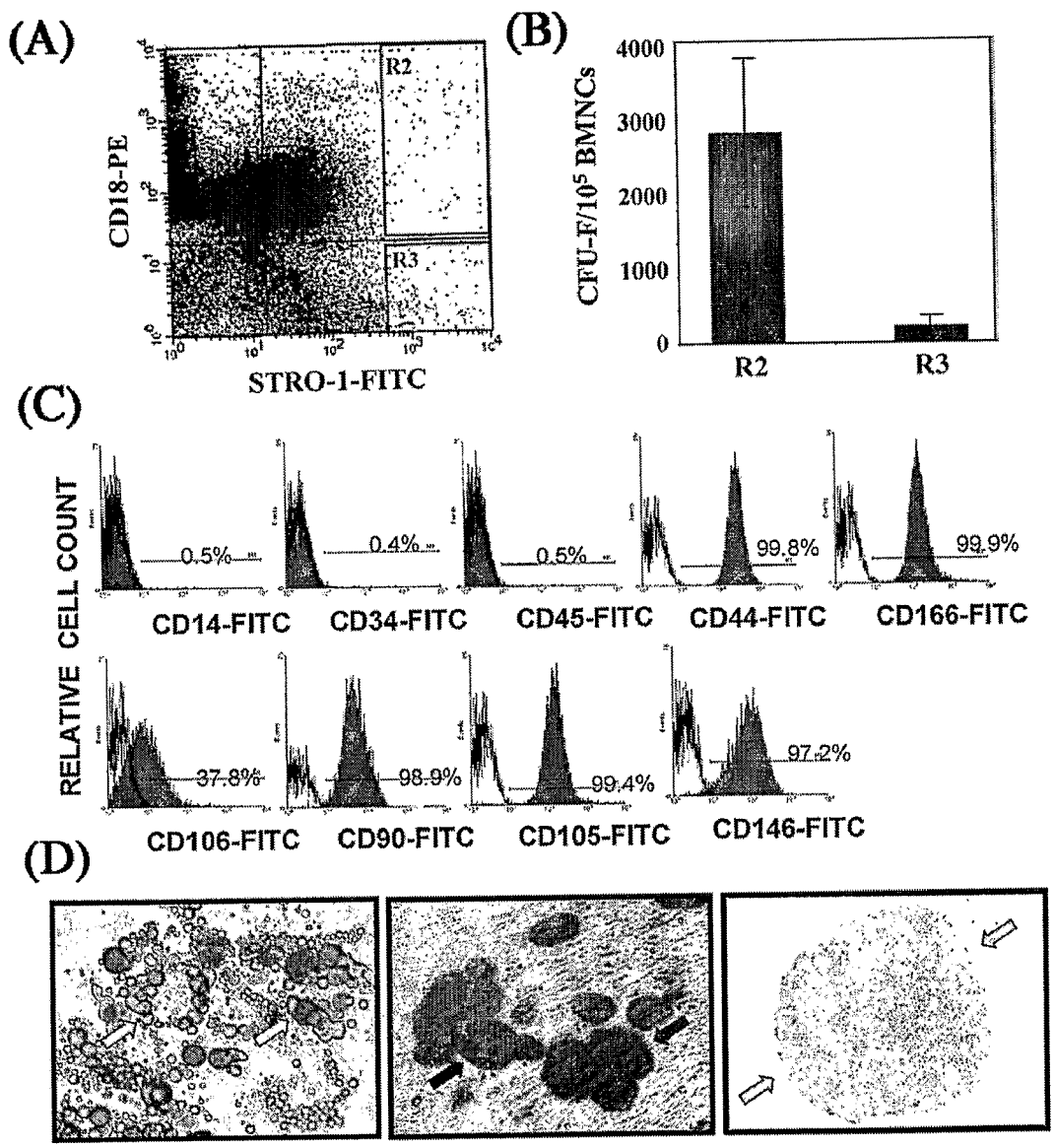
FIG. 2 shows FACS analysis of Human STRO-1$^{bright}$/CD18 + BMSSCs.

Given the presence of CD18 on the BMSSCs, we tested the possibility of using CD18 as a selection marker for these mouse and human stem cells hBMSSCs were sorted from human bone marrow aspirates based on dual expression of CD18 (mAb 6.7) and the stromal stem cell marker, STRO-1 (5, 30, 32). (FIG. 2A). The number of BMSSCs among the sorted cells was determined by CFU-F assays (FIG. 2B). The results using dual-color FACS isolation showed that human bone marrow mononuclear cells (hBM) co-expressing CD18 and STRO-1 antigens (FIG. 2A, R2, CD18$^+$STRO-1$^{bright}$) resulted in a 15-fold enhancement in the total number of BMSSC colonies compared to selecting hBMSSCs based on the expression of STRO-1 alone. (FIG. 2B) shows the CD18-negative population (R3, CD18$^-$STRO1$^{bright}$). Phenotypic characterization of the CD18$^+$STRO-1$^{bright}$ cells showed that they expressed CD44, CD166, CD106, CD90, CD105, and CD146, but not CD45 (a leukocyte marker), CD14 (a macrophage marker), or CD34 (a hematopoietic stem cell marker) (FIG. 2C). These results are consistent with the dual-color FACS results for murine BMSSCs (FIG. 1A).

The number of stromal stem cells obtained in the CD18$^+$STRO-1$^{bright}$ population was 15-fold higher than that of the CD18$^-$STRO-1$^{bright}$ population, suggesting that only the CD18 expressing cells in the STRO-1$^{bright}$ population are capable of self-renewal. Most of the other surface markers for stromal stem cells, including STRO-1, CD106/VCAM-1, CD146/MUC-18, HOP-26, CD49A/integrin $\beta_1$ and SB-10/CD166 (30, 32, 28) are expressed both on progenitor and on differentiated mesenchymal cells.

In a preferred embodiment, a population of animal cells enriched in bone marrow stromal stem cells that express the CD18 antigen is produced by: obtaining a sample of bone marrow from the animal, selecting bone marrow mononuclear cells from the sample, contacting the bone marrow mononuclear cells of step (b) with a reagent that binds to the CD18 antigen under conditions that permit the reagent and the CD18 antigen to bind; and selecting the bone marrow mononuclear cells that are bound to the reagent, thereby obtaining the population of animal cells enriched in bone marrow stromal stem cells that express the CD18 antigen. In another preferred embodiment a population of animal cells enriched in bone marrow stromal stem cells are selected by: obtaining a sample of bone marrow from the animal, (b) selecting bone marrow mononuclear cells from the sample, (c) contacting the bone marrow mononuclear cells of step (b) with a first reagent that binds to the STRO-1 antigen under conditions that permit the first reagent and the STRO-1 antigen to bind; (d) selecting the bone marrow mononuclear cells that are bound to the first reagent, thereby obtaining bone marrow stromal stem cells that express the STRO-1 antigen, (e) contacting cells of step (d) with a second reagent that binds to the CD18 antigen under conditions that permit the second reagent and the CD18 antigen to bind, and (f) selecting cells of step (e) to obtain bone marrow stromal stem cells that express both the CD18 and STRO-1 antigens, thereby obtaining the population of animal cells enriched in bone marrow stromal stem cells.

Other stromal stem cell markers, including CD106/VCAM-1, CD146/MUC-18, HOP-26, CD49A/integrin $\beta_1$ and SB-10/CD166 (30, 32) can be used in combination with the CD18 selection marker to obtain enriched populations of BMSSCs. In these other multi-marker embodiments, BMSSCs expressing the one or more other stromal stem cell marker(s) can be selected first, and then these cells can be contacted with a reagent that binds to CD18 to facilitate separation of BMSSCs that express CD18 and one or more other markers. Alternatively, the cells can be contacted with all of the reagents that bind to selective BMSSC markers, and then selected.

BMSSCs Isolated Based on CD18 Expression are Pleuripotent

When cultured in specific differentiation-inducing conditions, the CD18$^+$STRO-1$^{bright}$ cells were capable of differentiating into adipocytes (FIG. 2D, panel a), osteoblasts (FIG. 2D, panel b), and chondrocytes (FIG. 2D, panel c). These results show that the BMSSCs isolated using the methods of the present invention based on selective expression of CD18 are pleuripotent and can cultured under conditions that permit them to mature, proliferate and differentiate to generate osteoblasts, chondrocytes and adipocytes. An embodiment of the invention is directed to osteoblasts, chondrocytes and adipocytes that differentiate from BMSSCs in vitro and their therapeutic use to treat diseases where normal osteoblasts, chondrocytes and adipocytes are needed. Cytokines like IL-3, IL-6, IL-7, and soluble proteins like flt-3, erythropoietin, and stem cell factor, all have been shown to act in concert to achieve differentiation down a specific pathway. It is thought precise combinations of growth factors, cytokines, and tissue localizaton could give rise to different differentiated stem cells populations.

Mice Lacking CD18 have Normal Skeletal Development but Exhibit Features of Osteoporosis.

Figure 3:
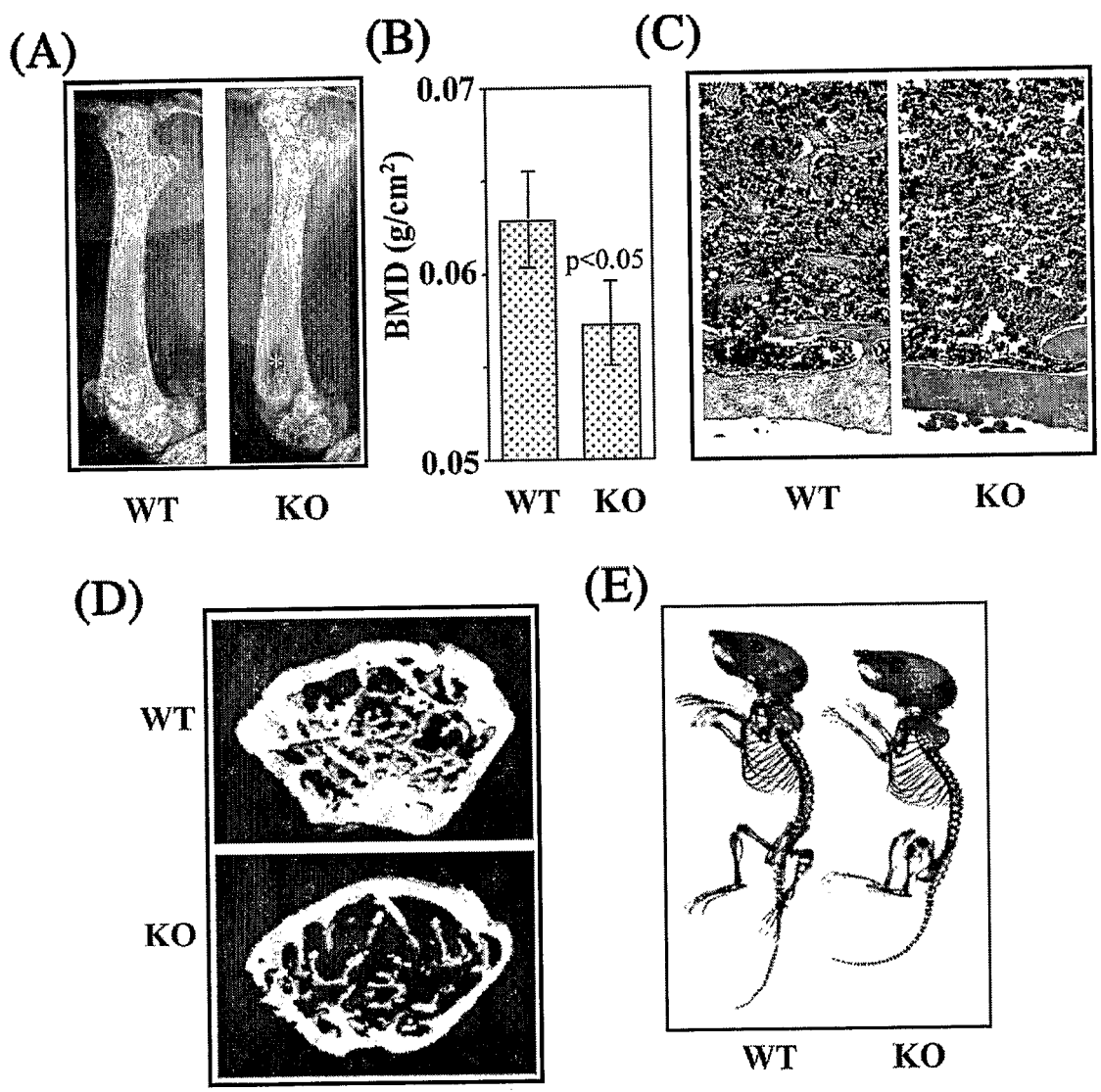
FIG. 3 shows phenotypic comparisons between CD18$^{-/-}$ mice and their WT sex-matched littermates.

To determine whether CD18 played a role in the function of BMSSCs, we examined bone phenotypes of the CD18$^{-/-}$ mice (Knockout or KO mice). Compared to their wild type (WT) sex-matched littermates, inactivation of the CD18 gene led to a significant (p<0.05) decrease in bone marrow density (BMD) of the femurs taken from both 5-week-old (n=3) and 15-week-old (n=4) mice, assessed by Faxitron (FIG. 3A) and DXA [dual-energy X-ray absorptimetry] (FIG. 3B). The bone defects did not exacerbate with age between 5 and 15 weeks (data not shown), showing that the reduced BMD in CD18-deficient animals was probably not caused by chronic inflammation. Histological analysis of the femurs demonstrated that CD18$^{-/-}$ mice had decreased trabecular bones in the distal metaphysis (FIG. 3C), and micro-computed tomography analysis of the distal femur metaphysis indicated that bone volume, trabecular bone number and trabecular bone thickness were diminished, and trabecular bone space was increased in CD18$^{-/-}$ mice (FIG. 3D and Table 1). Table 1 shows micro-computed tomography analysis of distal femoral metaphysis from five week old mice; scanning regions were confined to secondary spongiosa and were about 0.30 mm in thickness. Guided by the two-dimensional images, a region of interest was manually drawn near the endocortical surface. Trabecular bone morphometric indices, including bone volume relative to tissue volume (BV/TV, %), trabecular number (Tb.N), trabecular thickness (Tb.Th), and trabecular separation (Tb.Sp), were assessed based on the reconstructed three-dimensional images. No significant defect in skeletal development was observed in CD18$^{-/-}$ mice as compared to WT control mice (1-week-old) (FIG. 3E).

TABLE 1

MICRO-COMPUTED TOMOGRAPHY ANALYSIS OF DISTAL FEMORAL METAPHYSES FROM FIVE WEEK OLD MICE

|  | WILD TYPE | KNOCK OUT | P VALUE |
| --- | --- | --- | --- |
| BV/TV, % | 17.8 | 8.52 | 0.0041 |
| Tb.N,/mm | 15.78 | 341 | 0.012 |

TABLE 1-continued

MICRO-COMPUTED TOMOGRAPHY ANALYSIS OF DISTAL FEMORAL METAPHYSES FROM FIVE WEEK OLD MICE

|  | WILD TYPE | KNOCK OUT | P VALUE |
| --- | --- | --- | --- |
| Tb.Th,/um | 31 | 25 | 0.022 |
| Tb.Sp,/um | 151 | 348 | 0.035 |

CD18 Deficiency Does not Affect Overall Osteoclastic Activity.

Proper bone integrity is maintained through a balance between osteoclast-mediated bone resorption and osteoblast-mediated bone formation (7), both of which require engagement of the integrin receptors. For example, chondrocyte-specific inactivation of integrin $\beta_1$ leads to diminished chondrocyte motility, defective cell proliferation, and compromised chondrocyte-dependent endochondral bone formation (8). Mice deficient in integrin $\beta_3$ have normal osteoclastogenesis, but their mature osteoclasts are defective in ruffled membrane formation and bone resorption, resulting in osteopetrosis (9). Finally, deficiency of $\alpha_L\beta_2$, one of the four CD18 ($\beta_2$) integrins, affects osteoclast progenitor cell adhesion to the stromal cells, resulting in diminished osteoclastogenesis (10). Deficiency of all CD18 integrins could result in two opposite phenotypes: increased number of osteoclasts in the CD18-deficient mice due to severe leukocytosis (11), and defective osteoclastogenesis due to lack of one or more than one of the CD18 integrins. To test this hypothesis, we carried out quantitative measurement of in vivo osteoclastic activity, based on the serum concentration of the C-terminal telopeptides of type 1 collagen, a commonly used marker for bone resorption (24). No significant difference between CD18-deficient and WT mice was observed (FIG. 4A). To further evaluate the effect of CD18 deficiency on osteoclast formation, the total number of mature osteoclasts in the long bones of CD18$^{-/-}$ mice was quantified by TRAP staining (FIG. 4B). No difference was found between CD18-deficient and WT mice. The above data suggests that osteoclast-mediated bone resorption is probably not responsible for the decreased bone formation in the CD18$^{-/-}$ mice.

CD18 is Important for BMSSC Differentiation but not for Proliferation.

We hypothesized that genetic inactivation of CD18 impairs osteogenic activity of the BMSSCs, leading to the observed decreased bone formation. To test this hypothesis, in vitro mineralization induction assays were performed on both WT and CD18$^{-/-}$ BMSSCs. It was discovered that mineralization by the CD18$^{-/-}$ BMSSCs was significantly lower (p<0.01) than that by WT cells. FIG. 5A shows in vitro that mineralization induction of CD18$^{-/-}$ BMSSCs determined by Alizarin red S staining (magnification ×10), was significantly lower than that of WT cells (p=0.00003, n=3 mice). The total mineralized area by WT cells was assigned to 100%. In addition, CD18$^{-/-}$ BMSSCs adhered poorly to tissue culture dishes compared to their WT counterparts as is shown in FIG. 5B. Cells were allowed to adhere for 3 hours at 37° C. After washing, the adherent cells were counted manually based on 10 randomly picked view fields and expressed as a percentage of WT cell adhesion. (p=0.03, n=4). Interestingly, CD18-deficient BMSSCs proliferated better than the WT cells (p=0.01) based on BrdU incorporation assays determined manually by counting 10 representative fields (FIG. 5C). Moreover, the bone marrow from CD18$^{-/-}$ mice contained higher numbers of single colony-derived BMSSCs (CFU-F) (p<0.01) than that from WT mice (FIG. 5D: (p=0.0064, n=6 mice). Magnification ×10.

Figure 4:
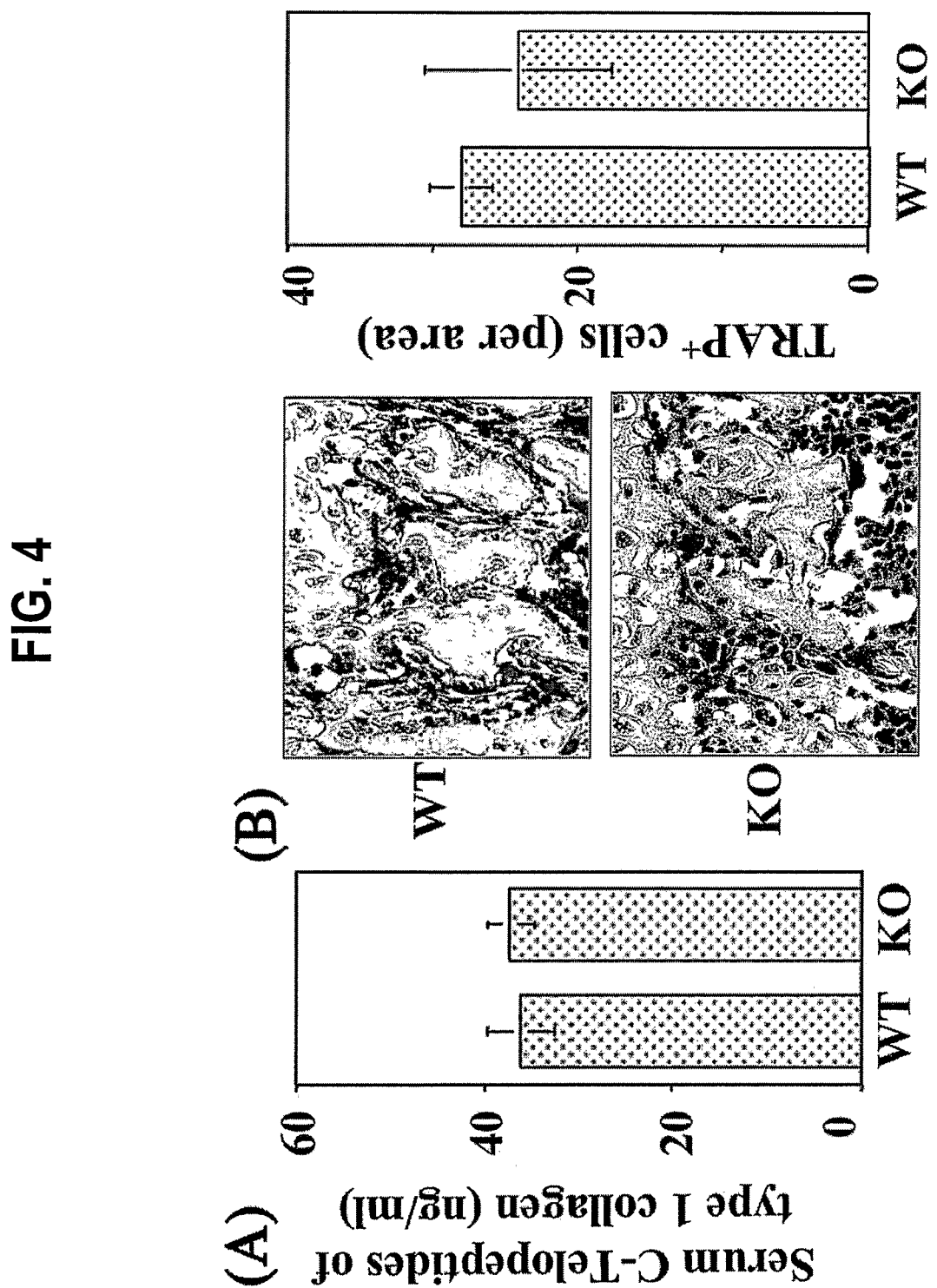
FIG. 4A shows CD18$^{-/-}$ in vivo osteoclastic activity determined by the serum concentration of C-terminal telopeptides of type 1 collagen in WT and CD18 deficient mice ($p=0.68$, $n=3$ mice).
FIG. 4B shows the number of mature osteoclasts in the femurs of the WT and CD18$^{-/-}$ mice determined by TRAP staining. ($p=0.13$, $n=4$ mice). Magnification ×200.
Figure 5:
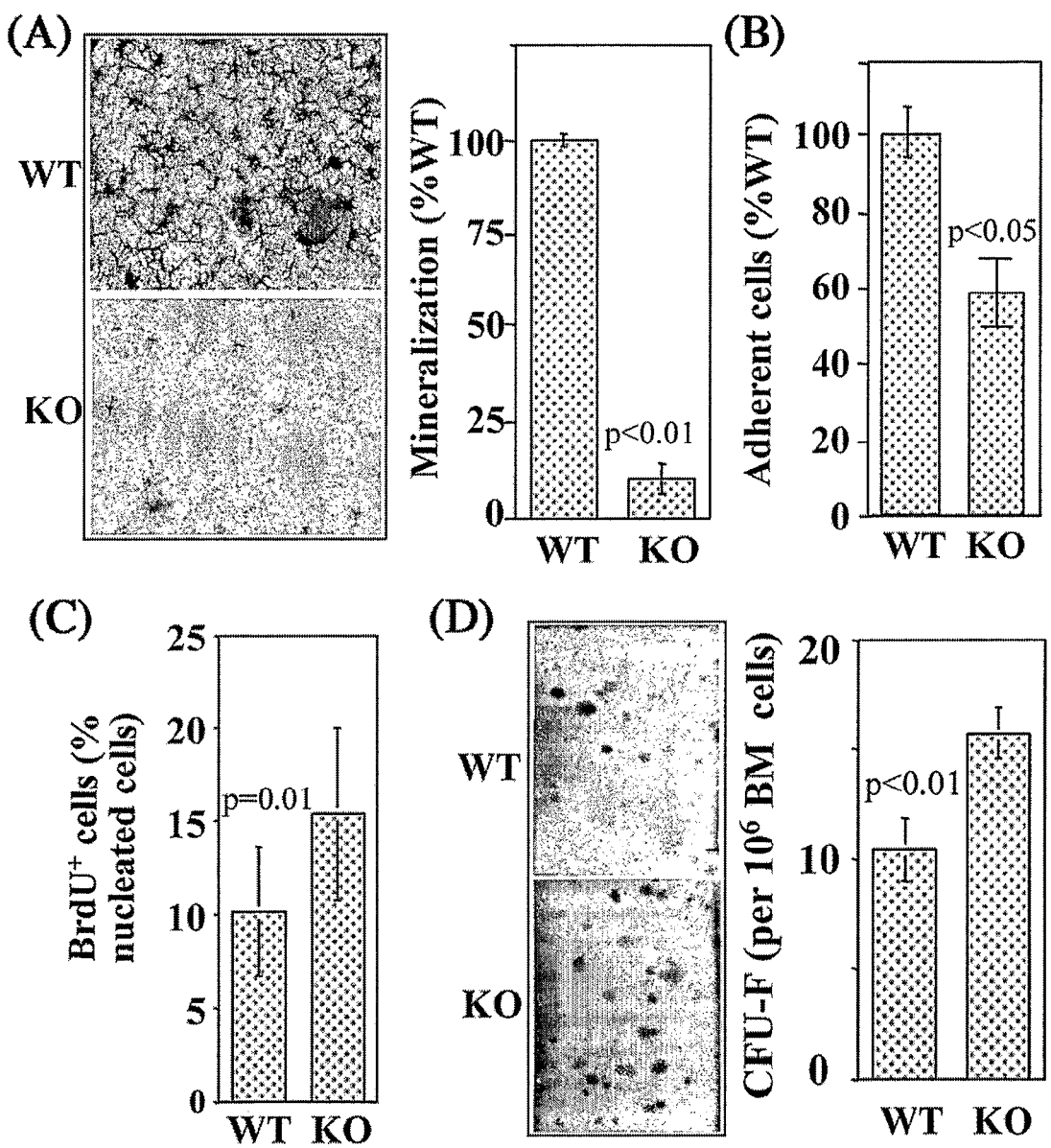

In addition to CD18, another known HSC marker Sca-1 is also expressed on stromal stem cells (29). Deficiency of Sca-1 leads to defects in HSC renewal (34) and mesenchymal stem cell renewal (35). As a result, Sca-1-deficient mice exhibit signs of osteoporosis, caused by both reduced bone formation and decreased bone resorption (35). Unlike Sca-1, CD18 deficiency affected the differentiation but not proliferation of BMSSCs (FIG. 5). Whether CD18 deficiency also affects the differentiation and renewal of HSC is currently unclear and needs further investigation. It has been reported that CD18 deficiency causes severe leukocytosis (11), which may potentially lead to increased number of osteoclast precursor cells in CD18 deficient mice. However, the defective expression of $\alpha_L\beta_2$ (one of the four CD18 integrins) in CD18$^{-/-}$ mice also decreases osteoclastogenesis (10). As a result, the overall osteoclastic activity in the CD18$^{-/-}$ mice remains unchanged (FIG. 4).

Figure 6:
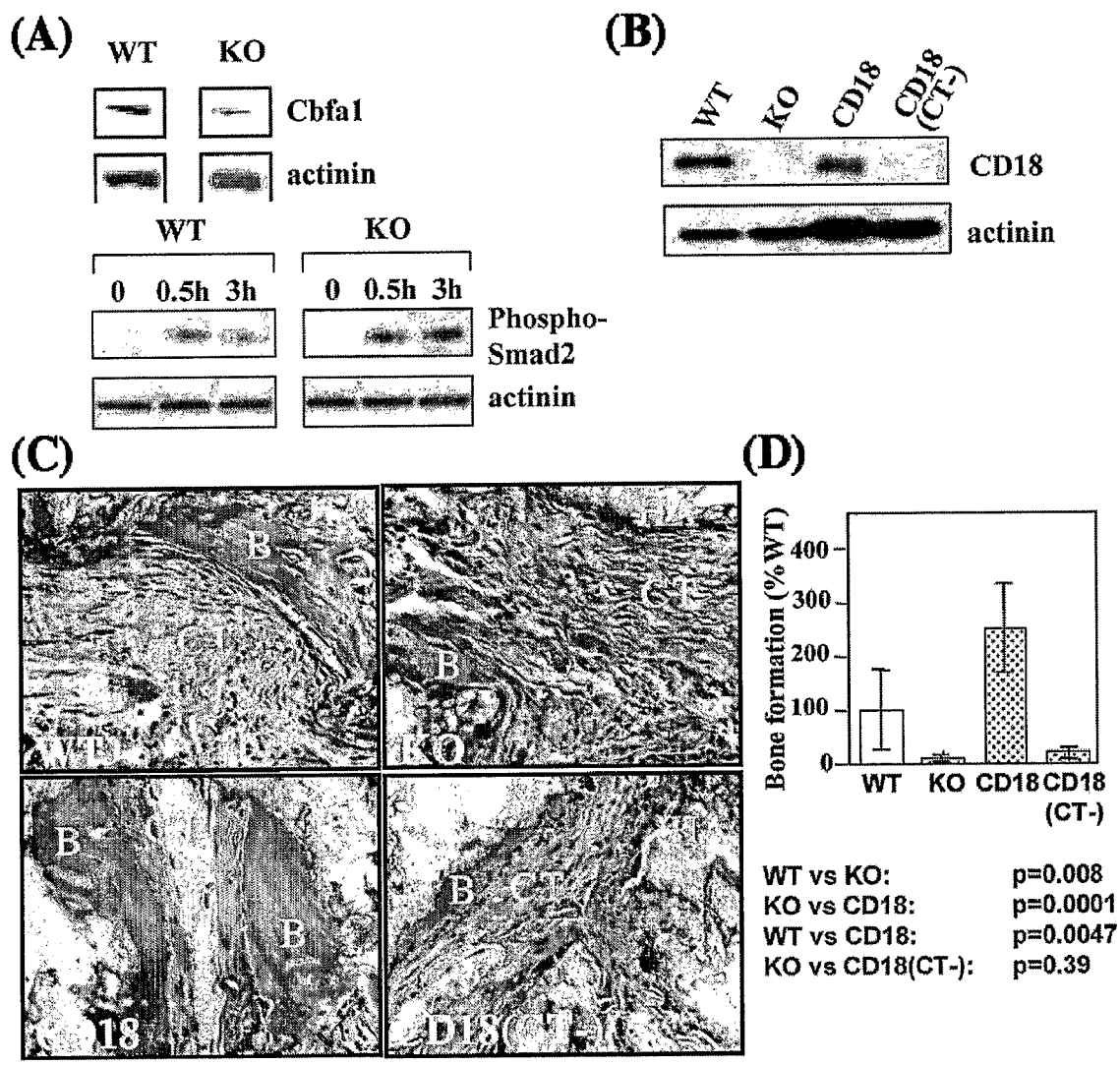

Cbfa1 (Runx2/AML3/PEBP2αC) is a master regulatory gene in osteogenesis (13), and its biological effects are regulated by transforming growth factor-β (TGF-β) through the Smad pathway (14, 15). TGF-β negatively regulates bone formation by inhibiting Cbfa1 expression and therefore the differentiation of osteoprogenitors through the Smad pathway. It was discovered that Cbfa1 expression in CD18$^{-/-}$ BMSSCs (Knock Out Mutants, KO) was decreased compared with that of WT BMSSCs (FIG. 6A, top panel). In addition, Smad2 phosphorylation was increased in response to TGF-β treatment in CD18$^{-/-}$ KO BMSSCs (FIG. 6A, lower panel). These results indicate that defective osteogenesis seen in CD18-deficient BMSSCs is associated with compromised Cbfa1 expression.

To further confirm the critical role of CD18 in BMSSCs-mediated osteogenesis, and to exclude the possibility that CD18 contributes indirectly to osteogenesis through its function in haematopoetic cells, we conducted function-rescue experiments. In these experiments CD18-deficient BMSSCs were transformed with vectors having either full length or cytoplasmic domain-truncated (CT-) CD18. Similar to WT BMSSCs, no macrophage contamination was detected in the P0 CD18$^{-/-}$ BMSSCs by FACS analysis (data not shown). To express recombinant CD18, the CD18$^{-/-}$ BMSSCs were infected with retroviruses having either full-length CD18 or mutant truncated CD18 (CT-). Expression of recombinant CD18 on BMSSCs was confirmed 6 days after infection by immunoblot, using a polyclonal antibody against the cytoplasmic tail of CD18 (FIG. 6B). The osteogenic capability of WT BMSSCs, CD18$^{-/-}$ BMSSCs and the two different CD18-expressing CD18$^{-/-}$ BMSSCs was evaluated using an in vivo model of ectopic bone formation (23). Consistent with the decreased osteogenic activity of the CD18$^{-/-}$ BMSSCs in vitro (FIG. 5A), we found that the CD18$^{-/-}$ BMSSCs failed to support bone formation in vivo (FIGS. 6C and 6D; WT vs KO, p=0.016). Bone formation was restored by the expression of full length CD18 in the CD18$^{-/-}$ BMSSCs (KO vs CD18, p=0.0001).

Surprisingly, transformed BMSSCs expressing CD18 constitutively using the retroviral promoter exhibited significantly higher in vivo osteogenic activity (~3-fold over WT BMSSCs; WT vs CD18, p=0.0047). This indicates that prolonged expression of CD18 in BMSSCs enhances osteogenesis. In contrast, cells transformed with the cytoplasmic domain-truncated CD18 failed to rescue the defective phenotype of bone formation (KO vs CD18 (CT-), p=0.39), showing that the cytoplasmic domain of CD18, which is required for integrin "outside-in" signaling, is also required for the osteogenic differentiation of the BMSSCs. Therefore an embodiment of the invention is directed to a method for treating bone degenerative diseases in an animal by administering BMSSCs from the animal that have been transformed with an expression vector to express CD18. The BMSSCs can be isolated from the animal or they can come from another animal of the same species. In all preferred embodiments, the animal is human.

Given the osteoporotic phenotype of the CD18$^{-/-}$ mice, the results show that patients with the severe form of LAD I, including those with restored HSC functions by gene therapy, could be predisposed to bone defects and the development of osteoporosis. Thus, it would be necessary to include reconstitution of CD18 expression on both HSCs and BMSSCs for gene therapy to treat LAD I patients. In an embodiment of the invention methods are provided for preventing or treating LAD I in an animal by administering a population of cells enriched in BMSSCs that have been transformed with a vector having a normal gene for CD18. In a preferred embodiment, the animal's own BMSSCs are isolated, transformed with an expression vector having gene for normal CD18, and reintroduced into the animal.

Table 1 shows micro CT analysis for distal femoral metaphyses from 5-wk-old mice by the use of μCT-20 (Scanco Medical, Bassersdorf, Switzerland). Scanning regions were confined to secondary spongiosa and were about 0.30 mm in thickness. Using 2-dimensional images, a region of interest was manually drawn near the endocortical surface. Trabecular bone morphometric indices, assessed using 3-dimensional image reconstructions, included bone volume relative to tissue volume (BV/TV, %), trabecular thickness (Tb.Th), trabecular number (Tb.N) and trabecular spacing (Tb.Sp). It was observed that prolonged expression of CD18 on BMSSCs significantly enhances osteogenesis and bone formation (FIG. 6D). Therefore increasing CD18 expression in BMSSCs by transforming them with retroviruses having the CD18 gene is beneficial to tissue engineering of bone and bone marrow. An embodiment of the invention is thus directed to the use of BMSSCs transformed with a gene for CD18 in tissue engineering of bone and bone marrow.

To summarize, these results demonstrate that CD18 is a newly identified specific marker for both human and mouse BMSSCs that can be used to select a population of cells enriched in BMSSCs from bone marrow mononuclear cells from bone marrow aspirate. The data shows that combining the CD18 marker with other stromal stem cell markers (e.g. STRO-1 and VCAM-1)[4] in cell sorting significantly enriches the BMSSC population from unfractionated bone marrow aspirate.

At the functional level, CD18-deficient mice showed bone defects, including decreased BMD and compromised osteogenic differentiation of BMSSCs. These defects are associated with a decrease in expression of Cbfa1, due to increased Smad signaling in absence of CD18-mediated "outside-in" signaling. The osteogenic differentiation deficiency of the CD18-deficient BMSSCs was rescued by expressing full-length CD18 in the absence of cells of the hematopoietic origin. In humans, the lethal bacterial and fungal infections in patients with complete CD18 deficiency, the most severe form of Leukocyte Adhesion Deficiency I (LAD I), could mask potential bone defects. Patients with the severe form of LAD I, including those with restored HSC functions by gene therapy, are still predisposed to bone defects. Thus, it would be necessary to include reconstitution of CD18 expression on both HSCs and BMSSCs for therapeutic treatments of the LAD I patients in the future. Therefore an embodiment of the present invention is directed to treating patients with LAD I with gene therapy to introduce a gene for CD18.

Obtaining an Enriched Population of BMSCCs Based on CD18 Expression

Generally, separation of a heterogeneous population of cells, such as in a bone marrow aspirate into target (such as, CD18-positive) and non-target (such as, CD18-negative) fractions is rarely complete. For the purposes of the present invention, separation is considered to have been accomplished if the target fraction is comprised of at least about 20% precursor cells, more often about 50% precursor cells, and preferably about 70% precursor cells.

Precursor cells may be positively selected or negatively selected. By positive selection is meant the capture of cells by some means, usually immunological, on the basis of their expression of a specific characteristic or set of characteristics (usually an antigen(s) expressed at the cell surface). For example, CD18-positive cells can be positively selected by any of the above methods (except cytolysis, which would result in destruction of the desired cells) on the basis of their expression of the CD18 antigen utilizing an anti-CD18 antibody, such as the monoclonal antibodies 6.7 (commercially available from Pharmingen/BD Bioscience.

Negative selection means the exclusion or depletion of cells by some means, usually immunological, on the basis of their lack of expression of a specific characteristic or set of characteristics (again, usually a surface antigen). For example, CD18-positive cell scan be negatively selected by any of the above methods on the basis of their lack of expression of lineage-defining antigens utilizing antibodies to the lineage-defining non-CD18 antigens. By using a cocktail or mixture of monoclonal antibodies directed to red cell, platelet, granulocyte, lymphocyte, adipocyte, and/or tumor cell antigens it is possible to leave behind a population of cells which is highly enriched for CD18-positive cells. Numerous monoclonal and polyclonal antibodies suitable for this purpose are known in the art and are commercially available from a wide variety of sources (for example, Becton Dickinson Co., Mountain View, Calif.; Coulter Immunology, Hialeah, Fla.; Ortho Diagnostics, Raritan, N.J., etc.).

Alternatively, BMSCCs can be separated from mature cells by a combination of negative and positive selection techniques. For example, there can be a first selection for CD18-positive cells utilizing an anti-CD18 antibody, followed by a second selection for lineage-negative/CD18-positive cells, using an anti-lineage antibody kit from BD Bioscience and deletion using magnetic beads. The advantage of this or other dual selection strategies is that the volume of cells which is placed into culture is smaller and thus more manageable.

Although selection of CD18-positive cells usually involves the use of one or more antibodies or fragments thereof, in some cases selection may involve the use of lectins or other types of receptors or ligands expressed on the cell surface.

Some methods and devices for the selection of BMSSCs from a mixture of non-target and target cells, involve labeling the target cells, directly, or indirectly, with a biotinylated antibody to one or more target cell surface antigens (CD-18 and STRO 1). Labeled cells are separated from unlabeled cells by flowing them through a bed of immobilized avidin, the labeled cells binding to the avidin by virtue of the biotinylated antibody bound to their surface, while the unlabeled cells pass through the bed. After washing the bed material, the labeled (bound) cells can be eluted from the bed, for example, by mechanical agitation.

The conventional MACS procedure is described by Miltenyi et al., "High Gradient Magnetic Cell Separation with MACS," Cytometry 11:231-238 (1990). To sort cells by MACS, one labels cells with magnetic beads and passes the cells through a paramagnetic separation column. The separation column is placed in a strong permanent magnet, thereby creating a magnetic field within the column. Cells that are magnetically labeled are trapped in the column; cells that are not pass through. One then elutes the trapped cells from the column.

According to the methods of the present invention, BMSSCs can be separated from bone marrow by bringing the aspirate into contact with one or more antibodies (polyclonal and/or monoclonal) against CD18 (integrin $\beta_2$). Cells that have been bound by the monoclonal antibody are then separated from unbound cells by any means known to those skilled in the art.

Various methods of separating antibody-bound cells from unbound cells are known. For example, the antibody bound to the cell (or an anti-isotype antibody) can be labeled and then the cells separated by a mechanical cell sorter that detects the presence of the label. Fluorescence-activated cell sorters (FACS) are well known in the art. In one preferred embodiment, the anti-stem cell antibody is attached to a solid support. Various solid supports are known to those of skill in the art, including, but not limited to, agarose beads, polystyrene beads, hollow fiber membranes, polymers, and plastic petri dishes Cells that are bound by the antibody can be removed from the cell suspension by simply physically separating the solid support from the cell suspension.

Selective cytophoresis can be used to produce a cell suspension from mammalian bone marrow cells. For example, marrow can be harvested from a donor (the patient in the case of an autologous transplant; a donor in the case of an allogeneic transplant) by any appropriate means. The marrow can be processed as desired, depending mainly upon the use intended for the recovered cells. The suspension of marrow cells is allowed to physically contact, for example, a solid phase-linked monoclonal antibody that recognizes an antigen on the desired cells, such as CD18. The solid phase-linking can comprise, for instance, adsorbing the antibodies to a plastic, nitrocellulose, or other surface. The antibodies can also be adsorbed on to the walls of the large pores (sufficiently large to permit flow-through of cells) of a hollow fiber membrane. Alternatively, the antibodies can be covalently linked to a surface or bead, such as Pharmacia Sepharose 6MB macrobeads. The exact conditions and duration of incubation for the solid phase-linked antibodies with the marrow cell suspension will depend upon several factors specific to the system employed. The selection of appropriate conditions, however, is well within the skill of the art.

The unbound cells are then eluted or washed away with physiologic buffer after allowing sufficient time for the stem cells to be bound. The unbound marrow cells can be recovered and used for other purposes or discarded after appropriate testing has been done to ensure that the desired separation had been achieved. The bound cells are then separated from the solid phase by any appropriate method, depending mainly upon the nature of the solid phase and the antibody. For example, bound cells can be eluted from a plastic petri dish by vigorous agitation. Alternatively, bound cells can be eluted by enzymatically "nicking" or digesting a enzyme-sensitive "spacer" sequence between the solid phase and the antibody. Spacers bound to agarose beads are commercially available from, for example, Pharmacia.

The eluted, enriched fraction of cells may then be washed with a buffer by centrifugation and either cryopreserved in a viable state for later use according to conventional technology or immediately infused intravenously into the transplant recipient.

Procedures for separation include magnetic separation using antibody-coated magnetic beads and affinity chromatography or "panning" using antibody attached to a solid matrix (e.g. plate). Techniques providing accurate separation include fluorescence-activated cell sorters, which can have varying degrees of sophistication, such as having multiple color channels, low angle and obtuse light scattering detecting channels, or impedance channels. Dead cells can be eliminated by selection with dyes associated with dead cells e.g., (propidium iodide, LDS). Red blood cells can be removed by (for example) elutriation, hemolysis, or Ficoll-Paque gradients. Any technique can be employed that is not unduly detrimental to the viability of the selected cells.

Conveniently, antibodies can be conjugated with labels for a number of different purposes: e.g., magnetic beads to allow for ease of separation of a particular cell type, biotin, which binds with high affinity to avidin or streptavidin; fluorochromes, which can be used with a fluorescence activated cell sorter; haptens; and the like. Multi-color analyses can be employed with a FACS or in a combination of immunomagnetic separation and flow cytometry. Multi-color analysis is of interest for the separation of cells based on multiple surface antigens such as STRO-1 and/or CD18. Fluorochromes which find use in a multi-color analysis include phycobiliproteins, e.g. phycoerythrin and allophycocyanins; fluorescein, and Texas red.

In one embodiment of the invention, an antibody against CD18 is directly or indirectly conjugated to a magnetic reagent, such as a superparamagnetic microparticle (microparticle). Direct conjugation to a magnetic particle is achieved by use of various chemical linking groups as known in the art. For example, antibody can be coupled to the microparticles through side chain amino or sulfhydryl groups and heterofunctional cross linking reagents. A large number of heterofunctional compounds are available for linking to entities. A preferred linking group is 3(2-pyridyldithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, an anti CD18 antibody is indirectly coupled to magnetic particles. The antibody is directly conjugated to a hapten, and hapten-specific, second-stage antibodies are conjugated to the particles. Suitable haptens include digoxin, digoxigenin, FITC, dinitrophenyl, nitrophenyl, avidin, and biotin. Methods for conjugation of the hapten to a protein are known in the art, and kits for such conjugations are commercially available.

For separation or identification of stem cells or progenitor cells, an antibody is added to a bone marrow aspirate or to a suspension of BMNCs. The amount of an antibody necessary to bind a particular cell subset is empirically determined by performing a test separation and analysis. The cells and an appropriate antibody are incubated for a period of time sufficient for complexes to form, usually at least about five minutes, more usually at least about 10 minutes, and usually not more than one hour, more usually not more than about 30 minutes.

The cells can additionally be incubated with antibodies or binding molecules specific for other cell-surface markers known to be present or absent on BMSCCs, such as STRO-1. For example, STRO-1 is useful in the positive selection of stem cells. Various markers known to be absent on stem cells, such as CD3, CD4, CD8, CD14, CD15, and CD19, can be used for negative selection. The labeled cells are separated in accordance with the specific antibody preparation. Fluorochrome-labeled antibodies are useful for FACS separation and magnetic particles for immunomagnetic selection or particularly high gradient magnetic selection (HGMS). Exemplary magnetic separation devices are described in WO/90/07380, PCT/US96/00953 and EP438,520, herein incorporated by reference.

The purified cell population can be collected in any appropriate medium. Various media are commercially available and can be used, including Dulbecco's Modified Eagle Medium (DMEM), Hank's Basic Salt Solution (HBSS), Dulbecco's phosphate buffered saline (DPBS), RPMI, Iscove's modified Dulbeco's medium (IMDM), and phosphate buffered saline (PBS) with 5 mM EDTA, any of which can be supplemented with fetal calf serum (FCS), bovine serum albumin (BAD), or human serum albumin (HSA).

Once the desired cells have been isolated, they can be propagated by growing in conditioned medium, for example from stromal cells, or in media comprising maintenance factors supporting the proliferation of BMSSCs e.g., stem cell factor or combinations of interleukins. The medium employed for culturing cells is conveniently a defined enriched medium, such as IMDM or a mixture of IMDM and RPMI 1640, and will generally be composed of salts, amino acids, vitamins, beta-mercaptoethanol, streptomycin/penicillin and 10% fetal calf serum, and can be changed from time to time, generally at least once to twice per week. See Example 3.

The subject BMSSCs of the present invention find use in a variety of ways. In one embodiment BMSSCs are isolated from a patient before radiation or chemotherapy, cultured to multiply and readministered to the patient to reconstitute an irradiated host and/or a host subject to chemotherapy. In another embodiment, BMSSCs are cultured under conditions that permit their maturation, proliferation and differentiation into one or more selected lineages through specific different growth factors as described in Example 3. The BMSSCs can be used as a source to make osteoblasts, chondrocytes, adipocytes, and neural cells in vitro for reintroduction into the animal from which the BMSSCs were derived (autologous), or into another animal of the same species (heterologous). Our results showed that when cultured in specific differentiation-inducing conditions, the $CD18^+STRO-1^{bright}$ BMSSCs were capable of differentiating into adipocytes (FIG. 2D, panel a), osteoblasts (FIG. 2D, panel b), and chondrocytes (FIG. 2D, panel c), thus confirming their pleuripotent differentiation potentials. See Example 3. Such factors as erythropoietin, colony stimulating factors (e.g., GM-CSF, G-CSF or M-CSF), interleukins (e.g. IL-1, -2, -3, -4, -5, -6, -7, -8, -9, or -10), or the like, or stromal cells can be used to influence the growth and differentiation of BMSSCs cells.

The cells can also be used in the isolation and evaluation of factors associated with the differentiation and maturation of BMSSC cells, including reagents that specifically bind to the CD18 antigen. Thus, the cell scan be used in assays to determine the activity of media, such as conditioned media; to evaluate fluids for growth factor activity or involvement with dedication of lineages; or the like.

BMSS cells can be frozen at liquid nitrogen temperatures and stored for long periods of time, as they can be thawed and reused. The cells will usually be stored in 5% DMSO and 95% fetal calf serum. Once thawed, the cells can be expanded by use of growth factors or stromal cells associated with stem cell proliferation and differentiation.

The enriched mammalian BMSSCs can be used in therapeutic methods such as stem cell transplantation, as well as other methods that are readily apparent to those skilled in the art. For example, BMSSCs can be isolated from a patient using the methods described herein, they can be cultured to multiply and can then be administered to the same patient or to a different patient requiring by infusion in an amount sufficient to restore the patient's damaged or diminished BMSSCs. Since BMSSCs are pleuripotent, they can differentiate into osteoblasts, chondrocytes, adipocytes, and neural cells in situ if they are injected into bone, cartilage, fat or the nervous system, respectively. Precise, effective quantities can be readily determined by those skilled in the art and will depend, of course, upon the exact condition being treated by the therapy. In many applications, however, an amount containing approximately the same number of stem cells found in one-half to one liter of aspirated marrow should be adequate.

The use of a stem cell-specific antibody need not be limited to the purification of stem cells prior to a transfection procedure. With the goal of generating vectors for in vivo gene therapy, it has been proposed to engineer into the gene therapy vectors themselves, mechanisms by which the vector will recognize its target cell (and preferably only its target) within the context of the entire organism. See, Kasahara et al., Science 266:1373-1376 (1994); Michael & Curiel, Gene Therapy 1:223-232 (1994); Chatterjee et al., Ann. N.Y. Acad. Sci. 770:79-90 (1995); Schwarzenberger et al., Blood 87:472-478 (1996). By incorporating stem cell-specific antibodies against CD18 into a vector, it may be possible to generate vectors that will recognize and target stem cells in the patient's bone marrow. Specifically, the antibody could be incorporated into liposome vectors, (Hughes et al., Cancer Res 49:6214-6220 (1989); Wang & Huang, Biochemistry 28:9508-9514 (1989); Ahmad et al., Cancer Res 53:1484-1488 (1993)), poly-L lysine conjugate vectors (Michael & Curiel, supra; Schwarzenberger et al., supra), or into viral vectors, including but not limited to adenoviral vectors, retroviral vectors, (Russell et al., Nucleic Acids Res 21:1081-1085 (1993); Somia et al., Proc. Natl. Acad. Sci. USA 92:7570-7574 (1995)), and adeno-associated vectors (Chatterjee et al., supra), modified to express on the vector surface, the antibody itself or proteins which would bind the antibody to the vector surface (such as the Fc receptor).

In another embodiment for a method of in vivo gene therapy, diseases of the bone marrow may be corrected by the introduction of the normal gene for CD18 into the patient's abnormal human stem cells, which can then be transplanted into a patient's bone marrow. For a general review of the methodologies, see Friedmann, T., Science 244:1275-1281 (June 1989) and Lancet 1: 1271-1272 (Jun. 4, 1988), the entire contents of which are hereby incorporated by reference as if fully set forth herein, under 35 U.S.C. §119(e). Leukocyte Adhesion Deficiency is a genetic diseases associated with BMSSCs that do not express CD18 or that express mutant CD18. In one embodiment LAD is treated by introducing the wild-type gene for CD18 into BMSSCs derived from the animal having the disease, and the transformed BMSSCs are then be reintroduced into the animal to treat or prevent the disease. A therapeutic gene can be introduced into the population cells enriched for BMSSCs, isolated as above by any method known in the art including physical methods such as co-precipitation with calcium phosphate, electroporation or microinjection (e.g., U.S. Pat. No. 4,873,191), or using viral vectors such as adenoviral, or retroviral vectors. In the latter case, the DNA of the retrovirus is cut with a restriction enzyme and the human DNA containing the desired sequence is inserted and ligated. The retrovirus containing the insertion is then infected into the stem cells. The stem cells can then be assayed for production of the desired protein. See, e.g., U.S. Pat. No. 4,902,783. The entire contents of the above references are hereby incorporated by reference as if fully set forth herein, under 35 U.S.C. §119(e).

EXAMPLES

Example 1

Cell Culture and In Vitro Assays

Mice. The CD18 null and their sex-matched C57BL/6J littermates were obtained by breeding heterozygotes of the CD18-null mice. Scharffetter-Kochanek, K., Lu, H., Norman, K., van Nood, N., Munoz, F., Grabbe, S., McArthur, M., Lorenzo, I., Kaplan, S., Ley, K. et al. (1998) *J Exp Med* 188, 119-131 and Miura, M., et al. (J Clin Invest. 2004 December; 114 (12):1704-13), the entire contents of which are hereby incorporated by reference as if fully set forth herein, under 35 U.S.C. §119(e). The CD18 null mice have been backcrossed more than 10 generations into the C57BL/6J background. Immunocompromised bg-nu/nu-xid nude mice were purchased from Harlan Sprague-Dawley (Indianapolis, Ind.). Mice were maintained in sterile micro-isolator cages and all animal experiments were performed with the approval of the committee of the American Red Cross (protocols #407 and #447) and the National Institute of Dental and Craniofacial Research (protocol #04-317).

Mouse and Human BMSSCs Culture

Preparation and expansion of the mouse BMSSCs were performed based on a previously published method. Miura, M., et al. (J Clin Invest. 2004 December; 114 (12):1704-13). Mouse bone marrow (BM) cells ($1.5 \times 10^7$) harvested from long bones were seeded into 10 cm culture dishes (Corning, Corning N.Y.), incubated for 3 hours at 37° C. to allow attachment of adherent cells, and washed twice with PBS to remove non-adherent cells. BM cells ($1.5 \times 10^7$) from long bones of guinea pigs were then added as feeder cells. To prevent proliferation in culture, the feeder cells were γ-irradiated (Caesium-137) with 6,000 cGy by a Gammacell-1000 Irradiator (Atomic Energy of Canada Ltd. Ontario, Canada) prior to seeding. The mouse culture medium consisted of α-MEM (Gibco BRL; Invitrogen Corp. Grand Island, N.Y.), 20% fetal bovine serum (FBS; Equitech-Bio Inc. Kerrvile, Tex.), 2 mM L-glutamine, 100 U/ml penicillin and 100 µg/ml streptomycin (Biofluids Inc., Rockville, Md.), and 10 nM dexamethasone (Sigma-Aldrich, St. Louis, Mo.) and 55 µM 2-mercaptoethanol (Gibco BRL; Invitrogen Corp.). BMSSCs formed adherent colonies after 7-16 days of culture, which was designated as passage 0. Primary BMSSCs were lifted to disperse the colony-forming cells and seeded on freshly prepared culture dishes. These cells were passaged when they reached confluence and utilized for further experiments.

Human BMSSCs Culture. Human BM aspirates from healthy adult volunteers were purchased from AllCells, LLC (Berkeley, Calif.). BMSSCs constitute about 0.1% of bone marrow cells in aspirates. Bone marrow is typically aspirated from the iliac crest, but may be obtained from other sites (such as the sternum) if necessitated by prior or concurrent disease or therapy. To identify putative BMSSCs, single-cell suspension of $1 \times 10^6$ of bone marrow mononuclear cells (BMNCs) were seeded into 15 cm culture dishes (Falcon; BD Bioscience, San Jose, Calif.) and non-adherent cells were removed after 3 hours of incubation at 37° C. The adherent cells were cultured with α-MEM supplemented with 15% FBS, 100 µM L-ascorbic acid 2-phosphate (Wako Pure Chemical Industries Ltd, Osaka, Japan), 2 mM L-glutamine, and a combination of 100 U/ml penicillin and 100 μg/ml streptomycin. The human culture medium was changed on day 7 and 14, if the cells were not passaged by day 14. Subsequent passages were performed when the cells were approaching confluent. BMSSCs of the second to the fifth passages were utilized for further experiments unless specifically mentioned.

Colony-Forming Unit Fibroblast (CFU-F) Assay.

The CFU-F assay was performed as previously described. Kuznetsov, S. & Gehron, R. P. (1996) Calcif. Tissue Int. 59, 265-270. BMSSCs can also be detected by other colony-forming assays, such as CFU-GM and CFU-S assays (see, for example, Sutherland et al., in Bone Marrow Processing and Purging, A. P. Gee (ed.), Boca Raton: CRC Press (1991), pg. 155). The entire contents of all of the above references are hereby incorporated by reference as if fully set forth herein, under 35 U.S.C. §119(e).

Mouse BM cells ($1$-$5\times10^6$) harvested from long bones were seeded into T-25 culture flasks (Nalge Nunc, Rochester, N.Y.), incubated for 3 hours at 37° C. to allow attachment of adherent cells, and then rinsed twice with PBS to remove nonadherent cells. BM cells ($1.5\times10^7$) from long bones of guinea pigs were then added as feeder cells. To prevent proliferation in culture, the feeder cells were γ-irradiated (Caesium-137) with 6,000 cGy by a Gammacell-1000 Irradiator (Atomic Energy of Canada Ltd. Ontario, Canada) prior to seeding. Culture medium consisted of α-MEM, 20% FBS, 2 mM L-glutamine, 100 U/ml penicillin and 100 μg/ml streptomycin and 55 μM 2-mercaptoethanol. Adherent colonies were fixed with methanol between day 7 and day 16 and stained with an aqueous solution of saturated methyl violet (Sigma-Aldrich). The sorted human BMSSCs, either STRO-$1^{bright}$/CD18$^+$ or STRO-$1^{bright}$/CD18$^-$, were plated on the culture dishes. Colony forming efficiency assays were performed at day 14 of culture following staining of the cultures with 0.1% (w/v) toluidine blue in 1% paraformaldehyde. Colonies containing equal to or greater than 50 cells were counted as colonies under a dissecting microscope.

Cell Proliferation Assays.

The proliferation of BMSSCs was assessed by bromodeoxyuridine (BrdU) incorporation of the cells. Mouse BMSSCs were seeded at $5\times10^5$ cells on 2 well chamber slides (Nalge Nunc, Rochester, N.Y.), incubated with BrdU solution (Zymed, San Francisco, Calif.) for 20 hrs. The number of BrdU positive cells were detected using BrdU staining kit (Zymed, San Francisco, Calif.) according to the manufacturer's instruction with hematoxylin counter staining. For quantification of BrdU positive cells, ten representative images captured at 200× magnification were used to calculate BrdU positive cell number. Cell proliferation was shown as a percentage of BrdU-positive cells over total nucleated cells.

Cell Adhesion Assays.

Same numbers of WT and CD18$^{-/-}$ BMSSCs were seeded on treated plastic chamber slides (Nalge Nunc, Rochester, N.Y.) in the culture medium. After 3 hours of incubation, the chamber slides were gently washed with PBS twice to remove non-adherent cells and the number of adherent cells was determined by manual counting of five representative fields at 100× magnifications.

Western Blot Analysis.

Cells were lysed in M-PER extraction reagent (Pierce Chemical Co., Rockford, Ill.), and protein concentrations were measured using Bio-Rad Protein Assay (Bio-Rad Laboratories Inc. Hercules, Calif.). To examine CD18 expression in mouse BMSSCs, total cell lysates from the same number of WT, CD18$^{-/-}$, and CD18-reconstituted (with either full-length or cytoplasmic tail-truncated CD18) BMSSCs were applied onto NuPAGE gel (Invitrogen Corp. Carlsbad, Calif.) at ~$3\times10^4$ cells per lane. The separated proteins were transferred onto PVDF membranes (Millipore, Bedford, Mass.) and blocked with a solution containing 10 mM Tris-HCl [pH7.5], 154 mM NaCl, 4% BSA, 1% milk, and 0.05% Tween-20 for 60 min at room temperature (RT). After washing, the membrane was incubated with rabbit anti-CD18 cytoplasmic tail antibodies (1:1000 dilution) in incubation buffer (10 mM Tris-HCl [pH7.5], 154 mM NaCl, 0.5% BSA, 0.05% Tween 20) for 60 min at RT. The membranes were then washed and incubated with a horseradish peroxidase (HRP)-conjugated goat anti-rabbit IgG (Santa Cruz Biotechnology Inc., Santa Cruz, Calif.) at 1:5,000 dilutions in incubation buffer for 30 min at RT. After washing with T-TBS, the membranes were reacted with HRP substrate (Pierce Chemical Co.) to visualize positive bands on x-ray films (Eastman Kodak Co., Rochester, N.Y.). To examine CD18 expression in human BMSSCs, total cell lysates from human BMSSCs at different passages were prepared. In each lane, twelve micrograms of protein were loaded and analyzed as described above. To examine Cbfa1 expression, 2.2 μg of total protein lysate from WT or CD18$^{-/-}$ BMSSCs were applied to NuPAGE and detected by immunoblot using rabbit anti-Cbfa1 (Oncogene Research Products, Cambridge Mass.) antibody at 1:500 dilution. To examine the effect of TGF-treatments, mouse BMSSCs were serum-starved with α-MEM supplemented with 2% FBS for 16 hours and then treated with 2 ng/ml TGF-β (R&D Systems Inc. Minneapolis, Minn.) for the indicated periods. Phosphorylation of Smad2 was examined by loading equal amount of cell lysate (12 μg) in each lane and detected by immunoblot using rabbit anti-phospho-Smad2 antibody (Cell Signaling Technology Inc., Beverly, Mass.) at 1:500 dilution. Each membrane was also stripped using the stripping buffer (Pierce Chemical Co.) and re-probed with mouse anti-α-actinin mAb (Upstate, Lake Placid, N.Y.) or anti-β-actin (Sigma-Aldrich) to quantify the amount of proteins loaded.

Example 2

Enrichment of hBMSSCs by Fluorescence-activated Cell Sorting

Detailed procedures for enrichment of the BMSSC population by cell sorting have been published (5), Gronthos, S. et al., Blood 84, 4164-4173 (1994) the entire contents of which are hereby incorporated by reference as if fully set forth herein, under 35 U.S.C. §119(e). and (3, 4). Bone marrow (BM) aspirates were provided by AllCell. Inc. To obtain the, 25 ml bone marrow was aspirated by board-certified physicians from a single site of the posterior iliac crest and withdrawn into a 60 cc syringe containing 15 ml of PBS plus 125 units heparin per ml of BM. Bone marrow mononuclear cells (BMNCs) were isolated from BM aspirates by density centrifugation over a Ficoll solution (Amersham).

Approximately $1$-$3\times10^8$ BMNCs were sequentially incubated with STRO-1 supernatant (IgM), anti-IgM -biotin, streptavidin microbeads and finally streptavidin-FITC (Caltag Laboratories, Burlingame, Calif.) before being separated on a Mini MACS magnetic column (Miltenyi Biotec Inc., Auburn, Calif.). The FITC-labeled STRO-1 positive BMNCs isolated by MACS were co-labeled with a mouse anti-human CD18 mAb (clone 6.7, Pharmingen/BD Bioscience) for 30 minutes on ice, washed and incubated with PE-conjugated goat anti-mouse IgG (Pharmingen/BD Bioscience) for an additional 20 min on ice. While this can be done in one step, better cell quality can be obtained using two steps. After washing, cells were sorted for both CD18 and STRO-1 using a FACStarPLUS flow cytometer (Becton Dickinson). The sorted human BMSSCs, either STRO-1bright/CD18+ or STRO-1$^{bright}$/CD18−, were used for further experiments.

Flow Cytometric Analysis of BMSSCs.

The sorted human STRO-1$^{bright}$/CD18+ BMSSCs were incubated with either of the primary antibodies or their corresponding isotype-matched control antibodies at a concentration of 10 μg/ml for one hour on ice. Primary antibodies: mouse IgG$_1$ anti-human CD14, CD34, CD45 (DAKO cytomation, Carpinteria, Calif.); mouse IgG$_1$ anti-human CD44 (H9H11) and IgG$_{2a}$ anti-human CD146 (CC9); mouse IgG$_1$ anti-human CD90, CD105, CD166 (Pharmingen; BD Bioscience, San Jose, Calif.); mouse IgG$_1$ anti-human CD106 (6G10) (kindly provided by Dr. B. Masinovsky, ICOS Corporation, Bothell, Wash.). Isotype-matched control mouse monoclonal antibodies: 1B5 (IgG$_1$) and 1A6.11 (IgG$_{2b}$) (kindly provided by Prof. L. K. Ashman, Medical Science Building, University of Newcastle, New South Wales, Australia). After washing, the cells were incubated with the secondary detection reagents, goat anti-mouse IgG$_1$- or IgG$_{2b}$-FITC conjugated antibodies (1/50) (Southern Biotechnology Associates Inc., Birmingham, Ala.) for 45 minutes on ice. Following washing, the samples were analyzed using an Epics®-XL-MCL flow cytometer (Beckman Coulter, Hialeah, Fla.). For dual-color FACS analysis of mouse BMSSCs, single cell suspension of P0 BMSSCs (1×10$^6$) were incubated with a pair of FITC- and PE-conjugated antibodies or their corresponding isotype-matched controls (each antibody at 10 μg/ml) for 45 min on ice. Following washing, the samples were analyzed using a FACScan flow cytometer (Becton Dickinson, San Jose, Calif.). The percentage of cell population in each quadrant was calculated using the FACScan program. All antibody conjugates were purchased from Pharmingen/BD Bioscience unless specifically mentioned, including PE-conjugated rat anti-mouse CD18 (C71/16, IgG2a), FITC- and PE-conjugated Sca-1 (E13-161.7, IgG2a), FITC-conjugated rat anti-mouse CD14 (rmC5-3, IgG1), FITC-conjugated anti-CD34 (49E81, IgG2a), and their corresponding FITC and PE-conjugated IgG controls.

Example 3

In vivo Osteoclast Activity

In vivo osteoclastic activity was determined by measuring the serum concentrations of c-terminal telopeptides of type 1 collagen, obtained from the peripheral blood of 8-week-old mice, using Ratlap ELISA kit (Osteometer BioTech A/S, Herlev, Denmark) according to the manufacture's instructions. The number of mature osteoclasts was determined by the tartrate-resistant acid phosphate (TRAP) staining, as previously described. Chiang, C. Y., Kyritsis, G., Graves, D. T. & Amar, S. (1999) *Infect Immun* 67, 4231-4236. Briefly, the left femurs were harvested from mice, fixed with 2% paraformaldehyde, decalcified with 10% EDTA (pH 8.0) and embedded in paraffin. Sections were deparaffinized, hydrated and stained for TRAP. The TRAP solution was a mixture of the following two solutions: 9.6 mg of naphthol AS-BI phosphate substrate (Sigma-Aldrich) dissolved in 0.6 ml of N,N-dimethylformamide and 84 mg of fast red-violet LB diazonium salt (Sigma-Aldrich), 58.2 mg of tartaric acid (Sigma-Aldrich), 240 μl of 10% MgCl2, 4 ml of 3 M sodium acetate buffer (pH 5.0) dissolved in 56 ml of distilled water. The mixture was passed through a 0.22 μm filter before us. The sections were incubated for 30 min in the TRAP solution at 37° C. in the dark and then washed with distilled water for 10 min, followed by a counterstaining with hematoxylin. For quantification of TRAP positive cells in the bones, 4 representative images were captured under microscope with a 200× magnification and then analyzed using the program NIH Image. The results were expressed as the number of TRAP positive cells per total bone area.

In Vitro Differentiation Potentials of the Sorted Human BMSSCs.

Osteogenic differentiation of the sorted human STRO-1$^{bright}$/CD18+ BMSSCs was induced in the presence of 100 μM L-ascorbate-2-phosphate, 3 mM inorganic phosphate and 10 nM dexamethasone. Calcium deposits were identified by Alizarin Red S staining after 3 weeks of cultivation. Gronthos, S., Graves, S. E., Ohta, S. & Simmons, P. J. (1994) *Blood* 84, 4164-4173. Adipogenesis was induced in α-MEM supplemented with 15% FBS, 100 μM L-ascorbate-2-phosphate, 0.5 mM isobutyl-methylxanthine, 0.5 μM hydrocortisone, 60 μM indomethacin and 10 μg/ml recombinant human insulin. Oil Red O staining was used to identify lipid-laden fat cells after 2 weeks of cultivation, as previously described. Gimble, J. M., Morgan, C., Kelly, K., Wu, X., Dandapani, V., Wang, C. S. & Rosen, V. (1995) *J. Cell Biochem.* 58, 393-402. Chondrogenic differentiation was amused by histochemical staining with Alcian blue (pH 1) in aggregate cultures treated with 100 μM L-ascorbate-2-phosphate, 2 mM sodium pyruvate, 1% insulin/transferring/selenous acid mixture (ITS; BD Biosciences), 100 nM dexamethasone and 10 ng/ml transforming growth factor β as described previously. Pittenger, M. F., Mackay, A. M., Beck, S. C., Jaiswal, R. K., Douglas, R., Mosca, J. D., Moorman, M. A., Simonetti, D. W., Craig, S. & Marshak, D. R. (1999) *Science* 284, 143-147.

Example 4

In Vitro Mineralization Induction of Mouse BMSSCs

For the mineralization induction of mouse BMSSCs in vitro, 2 mM μ-glycerophosphate (Sigma-Aldrich) and 100 μM L-ascorbic acid 2-phosphate (Wako Pure Chemical Industries Ltd, Osaka, Japan) were added to the mouse culture medium. After 6 weeks of cultivation, the cultures were stained with 1% alizarin red to examine calcium accumulation in the cells. The images were captured with a scanner (Epson, Tokyo, Japan) and mineralized areas were quantified using TotaLab software (Nonlinear Dynamics). Mineral deposits were expressed as a ratio relative to WT mouse BMSSC-mediated mineralization.

Example 5

Mouse BMSSC-mediated Bone Formation in vivo

Approximately 4.0×10$^6$ mouse BMSSCs were mixed with 40 mg hydroxyapatite/tricalcium phosphate (HA./TCP ceramic powder (Zimmer Inc, Warsaw, Ind.), and the mixture was implanted subcutaneously into the dorsal surface of 8 to 10 week-old immunocompromised bg-nu/nu-xid nude mice as previously described. Krelsbach, P. H., Kuznetsov, S. A., Satomura, K., Emmons, R. V., Rowe, D. W. & Robey, P. G. (1997) *Transplantation* 63, 1059-1069. The transplants were recovered 7 weeks after implantation and fixed with 2% paraformaldehyde, decalcified with 10% EDTA (pH 8.0) and embedded in paraffin. For quantification of bone formation in the transplants, sections were deparaffinized, hydrated and stained with hematoxylin and eosin. Five to seven representative fields at 50× magnification were selected for each BMSSC transplant. The total bone area within each field was calculated using the program NIH Image as previously described, and expressed as a percentage of bone formation by WT BMSSCs. Histological analysis and quantification of bone formation in the harvested implants was done as previously described Shi, S. et al. (23).

Analysis of Bone Phenotypes.

The CD18-deficient mice and their sex-matched C57BL/6J littermates at the age of 5- to 15-week-old were used to analyze bone phenotypes. Radiographs of left femurs were taken by Faxitron (Wheeling, Ill.). Quantitative analysis for bone mineral density (BMD) on left femurs was based on dual energy x-ray absorptiometry (DXA) by the use of a GE Lunar Piximus (GE Lunar, Madison, Mich.). Distal femoral metaphyses were analyzed by micro-computed tomography (μCT-20; Scanco Medical, Bassersdorf, Switzerland) as previously described. Miura, M., Chen, X. D., Allen, M. R., Bi, Y., Gronthos, S., Seo, B. M., Lakhani, S., Flavell, R. A., Feng, X. H., Robey, P. G. et al. (2004) *J. Clin. Invest* 114, 1704-1713. The scanning regions were confined to secondary spongiosa and were approximately 0.30 mm in thickness. Using 2-dimensional images, a region of interest was manually drawn near the endocortical surface. Cancellous bone morphometric indices were assessed using 3-dimensional image reconstructions, included bone volume/total volume (BV/TV) (%), trabecular thickness (Tb.Th), trabecular number (Tb.N), and trabecular separation (Tb.Sp). Peripheral quantitative computed tomography (pQCT) analysis of the distal femora was performed using an XCT Research M scanner (Stratec; Norland Co.) as previously described. Miura, M., et al. Briefly, scans were obtained at 2.25 mm and 2.75 mm from the distal condyles and cancellous BMD. Machine cancellous BMD precision (based on the manufacturer's data) was±3 mg/cm$^3$, while the coefficient of variation in our laboratory based on repeat scans was 2.26%. For histological analysis, left femurs were harvested from mice, fixed with 2% paraformaldehyde, decalcified with 10% EDTA (pH 8.0) and embedded in paraffin. Sections were deparaffinized, hydrated and stained with hematoxylin and eosin. To analyze the whole skeleton, one-week-old mice were dissected to remove skin, muscle and fat and kept in acetone to remove further fat for 3 days. They were then stained with 0.09% alizarin red S and 0.05% alcian blue in a solution containing ethanol, glacial acetic acid and water (67:5:28) for 48 hrs at 37° C. After staining, the mice were transferred to 1% potassium hydroxide until the skeleton was clearly visible. The mice were preserved in 100% glycerol with gradual increase in concentration.

Osteoclast Activity.

The tartrate-resistant acid phosphate (TRAP) staining was performed as previously described (25). Serum concentration of C-terminal telopeptides of type 1 collagen in mice was measured using Ratlap ELISA kit (Osteometer BioTech A/S, Herlev, Denmark).

Retroviral Meditated CD18 Expression in Mouse BMSSCs.

Murine CD18 cDNA was subcloned into the retroviral expression vector MGIN, using the EcoRI and NotI restriction sites. Cheng, L., Du, C., Murray, D., Tong, X., Zhang, Y. A., Chen, B. P. & Hawley, R. G. (1997) *Gene Ther* 4, 1013-1022. To achieve better expression, a Kozak sequence (ACCATGG) was inserted before the initiation codon of the CD18 protein. After confirming the correctness of the inserted CD18 sequence by DNA sequencing, the retroviral expression vector MGIN-CD18 was transfected into the packaging cell line GP+E-86, using Lipofectamine (Invitrogen). Markowitz, D., Goff, S. & Bank, A. (1988) *J. Virol.* 62, 1120-1124. Following G418 (600 μg/ml) selection of the transfected cells, individual clones were established by picking up single colonies and the titers of their viral supernatants were determined by infecting NIH3T3 cells and counting the colonies formed upon G418 selection. The clones that produce the highest retroviral titer (~1×10$^6$ colony-forming units/ml or CFU/ml) were used to prepare retroviral supernatants, which were subsequently concentrated to 6×10$^6$ CFU/ml and used to infect the CD18-deficient mouse BMSSCs in the presence of 8 μg/ml polybrene. Three days later, the medium was replaced with freshly prepared viral supernatants and the infected BMSSCs were used one day later for in vivo bone formation experiments. To evaluate the infection efficiency, a portion of the infected cells were kept for additional 3 days, and then analyzed by FACS analysis using a PE-conjugate of rat anti-mouse CD18 (mAb C71/16) and by immunoblot using a rabbit anti-CD18cytoplasmic domain antibody. Xiong, Y. M., Chen, J. & Zhang, L. (2003) *J Immunol* 171, 1042-1050.

Infection of the CD18-deficient mBMSSCs was performed by incubating the viral particles with subconfluent mBMSSCs in the presence of 8 μg/ml polybrene. Expression of the recombinant CD18 was assessed by FACS analysis and by RT-PCR.

Analytical Methods.

FACS analysis, immunoblot, cell adhesion assay, CFU-F assay, and BrdU labeling were conducted based on our published procedures (23, 27), and are described above.

Statistical Analysis.

Student's t test was used to analyze significance between 2 groups. A P value of less than 0.05 was considered significant.

All publications mentioned herein are incorporated herein by reference for the purpose of describing and disclosing, for example, the compounds and methodologies that are described in the publications which might be used in connection with the presently described invention. The publications discussed above and throughout the text are provided solely for their disclosure prior to the filling date of the present application. Nothing herein is to be construed as an admission that the inventors are not entitled to antedate such disclosure by virtue of prior invention.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

REFERENCE LIST

1. Zhang, J. et al. Identification of the haematopoietic stem cell niche and control of the niche size. *Nature* 425, 836-841 (2003).
2. Calvi, L. M. et al. Osteoblastic cells regulate the haematopoietic stem cell niche. *Nature* 425, 841-846 (2003).
3. Springer, T. A. Adhesion receptors of the immune system. *Nature* 346, 425-434 (1990).
4. Gronthos, S. et al. Molecular and cellular characterisation of highly purified stromal stem cells derived from human bone marrow. *J Cell Sci* 116, 1827-1835 (2003).

5. Gronthos, S., Graves, S. E., Ohta, S. & Simmons, P. J. The STRO-1+ fraction of adult human bone marrow contains the osteogenic precursors. *Blood* 84, 4164-4173 (1994).
6. Simmons, P. J. & Torok-Storb, B. Identification of stromal cell precursors in human bone marrow by a novel monoclonal antibody, STRO-1. *Blood* 78, 55-62 (1991).
7. Bianco, P. & Gehron, R. P. Marrow stromal stem cells. *J. Clin. Invest* 105, 1663-1668 (2000).
8. Aszodi, A., Hunziker, E. B., Brakebusch, C. & Fassler, R. Beta1 integrins regulate chondrocyte rotation, G1 progression, and cytokinesis. *Genes Dev.* 17, 2465-2479 (2003).
9. McHugh, K. P. et al. Mice lacking beta3 integrins are osteosclerotic because of dysfunctional osteoclasts. *J. Clin. Invest* 105, 433-440 (2000).
10. Tani-Ishii, N., Penninger, J. M., Matsumoto, G., Teranaka, T. & Umemoto, T. The role of LFA-1 in osteoclast development induced by co-cultures of mouse bone marrow cells and MC3T3-G2/PA6 cells. *J. Periodontal Res.* 37, 184-191 (2002).
11. Scharffetter-Kochanek, K. et al. Spontaneous skin ulceration and defective T cell function in CD18 null mice. *J Exp Med* 188, 119-131 (1998).
12. Bonde, M., Qvist, P., Fledelius, C., Riis, B. J. & Christiansen, C. Applications of an enzyme immunoassay for a new marker of bone resorption (CrossLaps): follow-up on hormone replacement therapy and osteoporosis risk assessment. *J. Clin. Endocrinol. Metab* 80, 864-868 (1995).
13. Komori, T. et al. Targeted disruption of Cbfa1 results in a complete lack of bone formation owing to maturational arrest of osteoblasts. *Cell* 89, 755-764 (1997).
14. Miyazono, K., Maeda, S. & Imamura, T. Coordinate regulation of cell growth and differentiation by TGF-beta superfamily and Runx proteins. *Oncogene* 23, 4232-4237 (2004).
15. Alliston, T., Choy, L., Ducy, P., Karsenty, G. & Derynck, R. TGF-beta-induced repression of CBFA1 by Smad3 decreases cbfa1 and osteocalcin expression and inhibits osteoblast differentiation. *EMBO J* 20, 2254-2272 (2001).
16. Schmalstieg, F. C. Leukocyte adherence defect. *Pediatr Infect Dis J* 7, 867-872 (1988).
17. Cheng, L. et al. A GFP reporter system to assess gene transfer and expression in human hematopoietic progenitor cells. *Gene Ther* 4, 1013-1022 (1997).
18. Bianco, P. & Robey, P. G. (2001) Nature 414, 118-121.
19. Krebsbach, P. H., Kuznetsov, S. A., Satomura, K., Emmons, R. V., Rowe, D. W. & Robey, P. G. (1997) Transplantation 63, 1059-1069.
20. Quarto, R., Mastrogiacomo, M., Cancedda, R., Kutepov, S. M., Mukhachev, V., Lavroukov, A., Kon, E. & Marcacci, M. (2001) N. Engl. J. Med. 344, 385-386.
21. Aszodi, A., Hunziker, E. B., Brakebusch, C. & Fassler, R. (2003) Genes Dev. 17, 2465-2479.
22. Miura. M., Chen, X. D., Allen, M. R., Bi, Y., Gronthos, S., Seo, B. M., Lakhani, S., Flavell, R. A., Feng, X. H., Robey, P. G. et al. (2004) J. Clin. Invest 114, 1704-1713.
23. Shi, S., Gronthos, S., Chen, S., Reddi, A., Counter, C. M., Robey, P. G. & Wang, C. Y. (2002) Nat. Biotechnol. 20, 587-591.
24. Kuznetsov, S. & Gehron, R. P. (1996) Calcif. Tissue Int. 59, 265-270.
25. Baron, R., Neff, L., Tran, V. P., Nefussi, J. R. & Vignery, A. (1986) Am J Pathol 122, 363-378.
26. Markowitz, D., Goff, S. & Bank, A. (1988) J Virol 62, 1120-1124.
27. Xiong, Y. M., Chen, J. & Zhang, L. (2003) J Immunol 171, 1042-1050.
28. Stewart, K., Monk, P., Walsh, S., Jefferiss, C. M., Letchford, J. & Beresford, J. N. (2003) Cell Tissue Res. 313, 281-290.
29. Van Vlasselaer, P., Falla, N., Snoeck, H. & Mathieu, E. (1994) Blood 84, 753-763.
30. Gronthos, S., Zannettino, A. C., Hay, S. J., Shi, S., Graves, S. E., Kortesidis, A. & Simmons, P. J. (2003) J Cell Sci 116, 1827-1835.
31. Simmons, P. J. & Torok-Storb, B. (1991) Blood 78, 55-62.
32. Shi, S. & Gronthos, S. (2003) J. Bone Miner. Res. 18, 696-704.
33. Bianco, P. & Gehron, R. P. (2000) J. Clin. Invest 105, 1663-1668.
34. Ito, C. Y., Li, C. Y., Bernstein, A., Dick, J. E. & Stanford, W. L. (2003) Blood 101, 517-523.
35. Bonyadi, M., Waldman, S. D., Liu, D., Aubin, J. E., Grynpas, M. D. & Stanford, W. L. (2003) Proc. Natl. Acad. Sci. U.S.A. 100, 5840-5845.
36. Papayannopoulou, T., Priestley, G. V., Nakamoto, B., Zafiropoulos, V., Scott, L. M. & Harlan, J. M. (2001) Blood 97, 1282-1288.

What is claimed is:

1. A method for selecting bone marrow stromal stem cells that express the CD18 antigen, comprising the steps of:
   (a) obtaining a sample of bone marrow from the animal,
   (b) selecting bone marrow mononuclear cells from the sample,
   (c) contacting the bone marrow mononuclear cells of step (b) with a first reagent that binds to the CD18 antigen under conditions that permit binding of said first reagent and the CD18 antigen, and
   (d) selecting the bone marrow mononuclear cells of step (c) that are bound to said first reagent, thereby obtaining the bone marrow stromal stem cells that express the CD18 antigen.

2. The method of claim 1, wherein said first reagent is an antibody that binds to the CD18 antigen.

3. The method of claim 1, further comprising the steps of:
   (e) contacting the bone marrow stromal stem cells of step (d) with a second reagent that binds to STRO-1 antigen under conditions that permit binding of said second reagent and the STRO-1 antigen; and
   (f) selecting the bone marrow stromal stem cells of step (e) that are bound to said second reagent, thereby obtaining bone marrow stromal stem cells that express the CD18 antigen, wherein said cells also express the STRO-1 antigen.

4. The method of claim 3, wherein said second reagent is an antibody that binds to the STRO-1 antigen.

5. The method according to claim 3, wherein step (f) is performed by a method chosen from the group consisting of fluorescence activated cell sorting, an immunomagnetic method, flow microfluorimetry, immunofluorescence, immunoperoxidase staining, radioimmunoassay and immunoaffinity chromatography.

6. The method according to claim 3, wherein said first reagent and said second reagent are each labeled with a fluorescent marker.

7. The method of claim 1, wherein step (c) further comprises contacting the bone marrow mononuclear cells of step (b) with a second reagent that binds to the STRO-1 antigen under conditions that permit binding of said second reagent and the STRO-1 antigen, and also wherein step (d) further comprises selecting the bone marrow mononuclear cells of step (c) that are bound to both said first and second reagents, thereby obtaining bone marrow stromal stem cells that express the CD18 antigen and the STRO-1 antigen.

8. The method of claim 7, wherein said second reagent is an antibody that binds to the STRO-1 antigen.

9. The method according to claim 1, wherein said first reagent is labeled with a fluorescent marker.

10. The method according to claim 9, wherein said fluorescent marker is fluoresceine isothiocyanate (FITC).

11. The method according to claim 1, wherein step (d) is performed by a method chosen from the group consisting of fluorescence activated cell sorting, an immunomagnetic method, flow microfluorimetry, immunofluorescence, immunoperoxidase staining, radioimmunoassay and immunoaffinity chromatography.

12. The method of claim 1, wherein said animal is human.

13. An isolated population of bone marrow stromal stem cells that express the CD18 antigen.

14. The isolated population of bone marrow stromal stem cells of claim 13, wherein said bone marrow stromal stem cells further express the STRO-1 antigen.

15. The isolated population of bone marrow stromal stem cells of claim 13, wherein said animal cells are human cells.

16. The isolated population of bone marrow stromal stem cells of claim 13, wherein said animal cells are derived from peripheral blood cells.

17. The isolated population of bone marrow stromal stem cells of claim 13, wherein said animal cells are derived from adipose tissue.

18. An isolated cell produced in vitro by the differentiation of the bone marrow stromal stem cells of claim 13, wherein said isolated cell is a cell type selected from the group consisting of osteoblasts, chondrocytes and adipocytes.

19. An isolated population of bone marrow stromal stem cells that express the CD18 antigen obtained according to the method of claim 1.

20. An isolated population of bone marrow stromal stem cells that express CD18 antigen and STRO-1 antigen obtained according to the method of claim 3.

* * * * *

UNITED STATES PATENT AND TRADEMARK OFFICE
CERTIFICATE OF CORRECTION

PATENT NO. : 7,732,126 B2
APPLICATION NO. : 11/574581
DATED : June 8, 2010
INVENTOR(S) : Zhang et al.

Page 1 of 1

It is certified that error appears in the above-identified patent and that said Letters Patent is hereby corrected as shown below:

Column 1, Lines 16-20, please replace the whole paragraph under "STATEMENT OF GOVERNMENTAL INTEREST" heading with the following:

This invention was made with government support under Grant Number HL061589 awarded by the National Institutes of Health. The government has certain rights in the invention.

Signed and Sealed this
Eleventh Day of September, 2012

David J. Kappos
*Director of the United States Patent and Trademark Office*